United States Patent
Komurata et al.

(10) Patent No.: US 10,691,203 B2
(45) Date of Patent: Jun. 23, 2020

(54) IMAGE SOUND OUTPUT DEVICE, IMAGE SOUND OUTPUT METHOD AND IMAGE SOUND OUTPUT PROGRAM

(71) Applicant: JVC KENWOOD Corporation, Yokohama-shi, Kanagawa (JP)

(72) Inventors: Miku Komurata, Yokohama (JP); Shuji Hakoshima, Yokohama (JP)

(73) Assignee: JVC KENWOOD Corporation, Yokohama-shi (JP)

( * ) Notice: Subject to any disclaimer, the term of this patent is extended or adjusted under 35 U.S.C. 154(b) by 13 days.

(21) Appl. No.: 15/955,941

(22) Filed: Apr. 18, 2018

(65) Prior Publication Data
US 2019/0073024 A1  Mar. 7, 2019

(30) Foreign Application Priority Data

Sep. 4, 2017  (JP) .................................. 2017-169667

(51) Int. Cl.

| | |
|---|---|
| *G06F 3/01* | (2006.01) |
| *G11B 27/031* | (2006.01) |
| *G06F 3/0484* | (2013.01) |
| *G06F 3/03* | (2006.01) |
| *G06F 3/16* | (2006.01) |
| *A61B 3/113* | (2006.01) |

(52) U.S. Cl.
CPC ............ *G06F 3/013* (2013.01); *G06F 3/0304* (2013.01); *G06F 3/0484* (2013.01); *G06F 3/04842* (2013.01); *G06F 3/165* (2013.01); *G11B 27/031* (2013.01); *A61B 3/113* (2013.01)

(58) Field of Classification Search
CPC ..... G11B 27/031; G06F 3/013; G06F 3/0484; G06F 3/0304; G06F 3/04842; G06F 3/165; A61B 3/113
USPC .............................. 348/14.01–14.16; 700/94
See application file for complete search history.

(56) References Cited

U.S. PATENT DOCUMENTS

| | | | | |
|---|---|---|---|---|
| 5,666,555 | A * | 9/1997 | Okazaki | ............. H04N 5/44591 348/E5.104 |
| 9,325,938 | B2 * | 4/2016 | Paragano | ............... H04N 7/141 |
| 2004/0001101 | A1 * | 1/2004 | Trajkovic | ................ G06F 3/147 715/781 |
| 2006/0256083 | A1 * | 11/2006 | Rosenberg | .............. G06F 3/013 345/156 |

(Continued)

FOREIGN PATENT DOCUMENTS

JP  2016-187589  11/2016

*Primary Examiner* — Hemant S Patel
(74) *Attorney, Agent, or Firm* — Amin, Turocy & Watson, LLP

(57) ABSTRACT

A gaze detection device includes a display screen configured to display an image; a sound output device configured to output a sound; a gaze point detector configured to detect a position of a point of gaze of an observer observing the display screen; an area setting unit configured to set a specific area on the display screen or part of the image; a determination unit configured to, when the specific area is set on the display screen or the image, determine whether the point of gaze is within the specific area on the basis of a result of the detecting the position of the point of gaze; and an output controller configured to cause the display screen to display the image and cause the sound output device to output the sound and adjust at least a mode in which the sound is output.

3 Claims, 17 Drawing Sheets

(56) References Cited

U.S. PATENT DOCUMENTS

| | | | | |
|---|---|---|---|---|
| 2008/0126976 | A1* | 5/2008 | Yukita | G11B 27/034 |
| | | | | 715/772 |
| 2011/0175932 | A1* | 7/2011 | Yu | G06F 3/013 |
| | | | | 345/661 |
| 2013/0300654 | A1* | 11/2013 | Seki | G06F 3/013 |
| | | | | 345/156 |
| 2014/0201805 | A1* | 7/2014 | Riordan | G06F 21/60 |
| | | | | 726/1 |
| 2015/0042552 | A1* | 2/2015 | Tsoref | G06F 3/013 |
| | | | | 345/156 |
| 2015/0243288 | A1* | 8/2015 | Katsuranis | G06F 3/0484 |
| | | | | 704/275 |
| 2017/0344108 | A1* | 11/2017 | Mosqueda Mejia | G06F 3/013 |

* cited by examiner

FIG.8

| ORDER | 1 | 2 | 3 | 4 | 5 | 6 |
|---|---|---|---|---|---|---|
| IMAGE NUMBER | IMAGE 1 | IMAGE 2 | IMAGE 3 | IMAGE 4 | IMAGE 5 | IMAGE 6 |
| REPRODUCTION TIME | t1 | t2 | t3 | t4 | t5 | t6 |

FIG.9

| SOUND | OUTPUT START SETTING | | OUTPUT END SETTING | | NUMBER OF TIMES OF OUTPUT |
|---|---|---|---|---|---|
| | IMAGE | TIME | SOUND/ IMAGE | TIME | |
| SOUND 1 | IMAGE 1 | 2 s | SOUND 1 | 10 s | ONCE |
| SOUND 2 | IMAGE 2 | 0 s | IMAGE 3 | 5 s | ONCE |

FIG.10

| SOUND | 1 | | 2 | | 3 | | 4 | |
|---|---|---|---|---|---|---|---|---|
| | TIME | VOLUME | TIME | VOLUME | TIME | VOLUME | TIME | VOLUME |
| SOUND 1 | 0 s | 50 | 10 s | 20 | 20 s | 50 | 30 s | 20 |
| SOUND 2 | 0 s | 0 | 0.5 s | 10 | 1 s | 20 | 1.5 s | 30 |

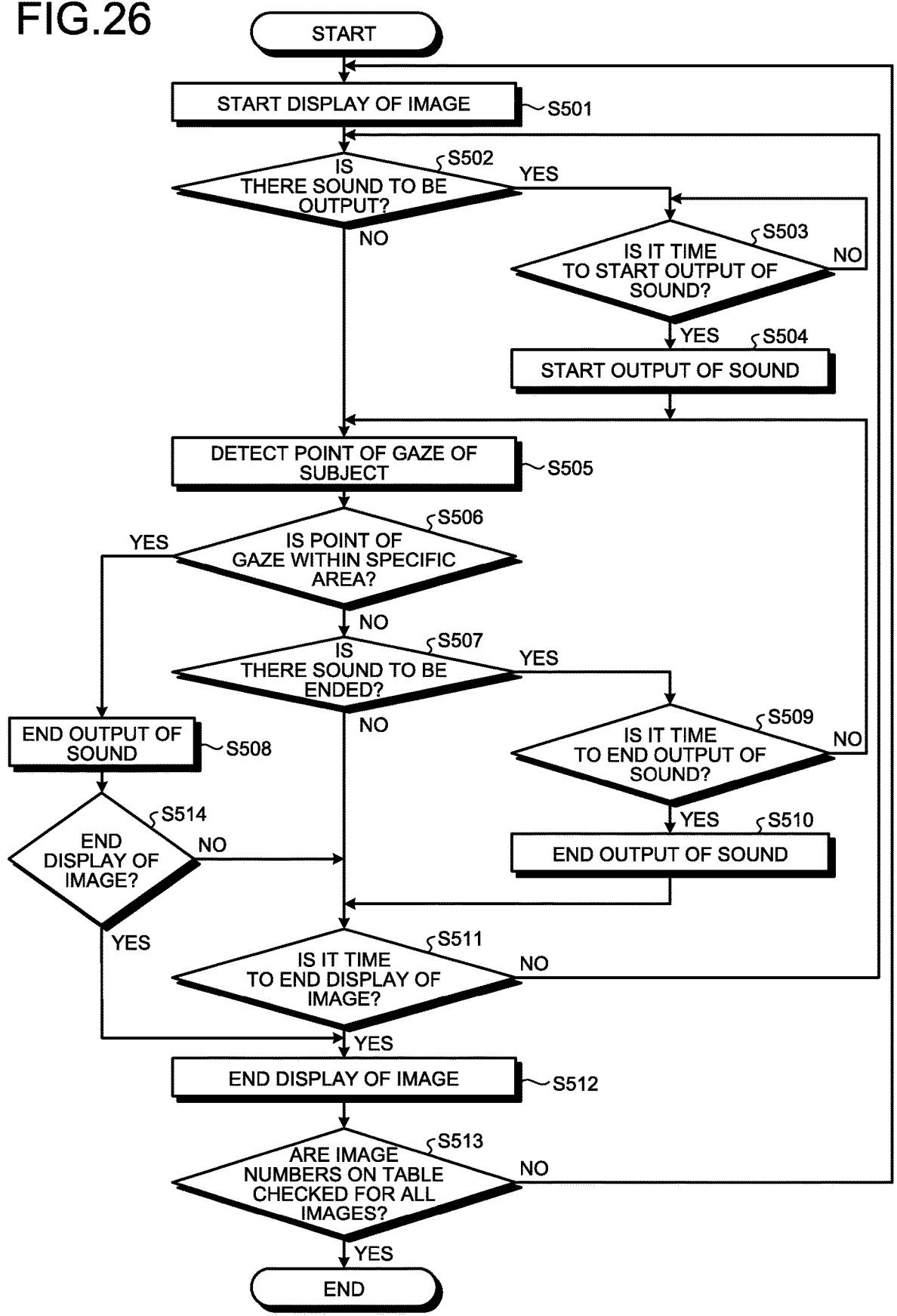

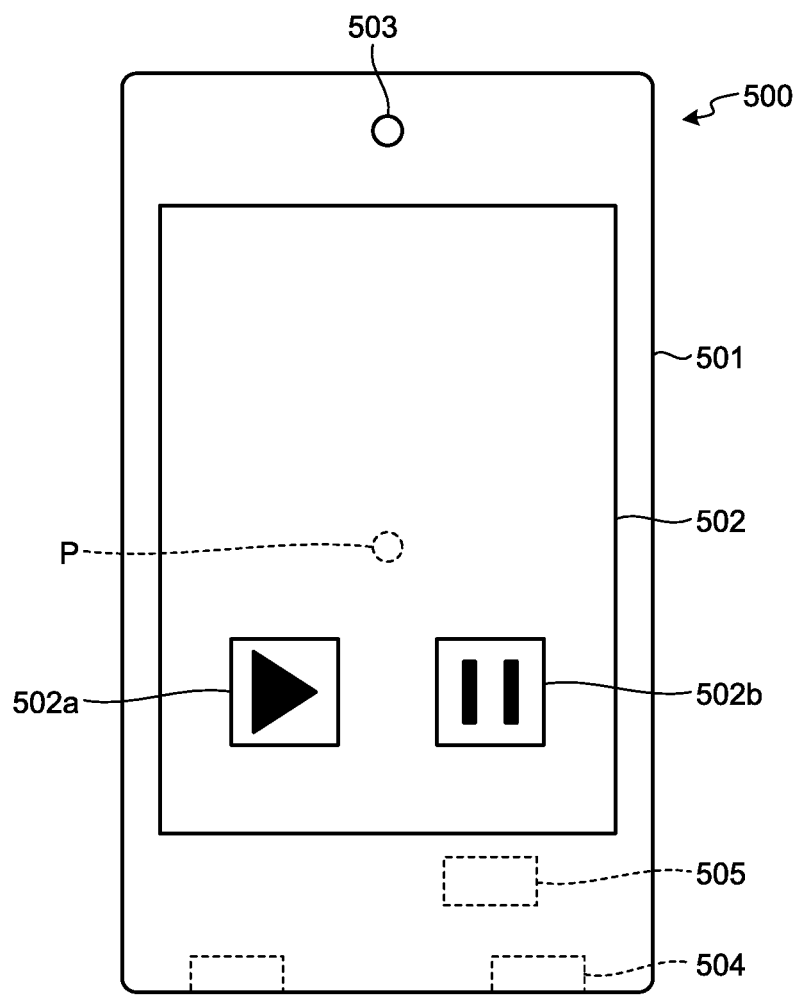

IMAGE SOUND OUTPUT DEVICE, IMAGE SOUND OUTPUT METHOD AND IMAGE SOUND OUTPUT PROGRAM

CROSS-REFERENCE TO RELATED APPLICATION(S)

The present application claims priority to and incorporates by reference the entire contents of Japanese Patent Application No. 2017-169667 filed in Japan on Sep. 4, 2017.

FIELD

The present disclosure relates to an image sound output device, an image sound output method and an image sound output program.

BACKGROUND

The corneal reflection technique is known as one of gaze detection technologies. The corneal reflection technique applies infrared light that is emitted from light sources to a subject, images, with cameras, the eyes of the subject to which the infrared light is applied, detects the positions of the pupils with respect to corneal reflection images that are reflected images of the light sources on the cornel surfaces, and detects the gaze of the subject. A gaze detection device using such a corneal reflection technique, for example, causes a display screen to display a still image or a moving image as a stimulus to a subject and causes a sound output device to output sound as the stimulus.

Patent Document 1: Japanese Laid-open Patent Publication No. 2016-187589 A

The above-described gaze detection device requires a configuration to efficiently adjust the timing of changing the mode in which sound is output. Furthermore, not only gaze detection devices but image sound output devices that output images and sounds require a configuration to efficiently adjust the timing of changing the mode in which sound is output.

SUMMARY

It is an object of the present disclosure to at least partially solve the problems in the conventional technology.

An image sound output device according to the present disclosure includes a display screen configured to display an image on a display screen, a sound output device configured to output a sound, a gaze point detector configured to detect a position of a point of gaze of an observer observing the display screen, an area setting unit configured to set a specific area on part of the display screen or of the image, a determination unit configured to, when the specific area is set on the display screen or the image, determine whether the point of gaze is within the specific area on the basis of a result of the detecting the position of the point of gaze, and an output controller configured to cause the display screen to display the image and cause the sound output device to output the sound and, when it is determined that the point of gaze is within the specific area, adjust at least a mode in which the sound is output.

An image sound outputting method according to the present disclosure includes causing a display screen to display an image, causing a sound output device to output a sound, detecting a position of a point of gaze of an observer observing the display screen, setting a specific area on part of the display screen or of the image, when the specific area is set on the display screen or the image, determining whether the point of gaze is within the specific area on the basis of a result of the detecting the position of the point of gaze, and when it is determined that the point of gaze is within the specific area, adjusting at least a mode in which the sound is output.

A non-transitory computer readable recording medium storing therein an image sound output program according to the present disclosure causes a computer to execute a process including causing a display screen to display an image, causing a sound output device to output a sound, detecting a position of a point of gaze of an observer observing the display screen, setting a specific area on part of the display screen or of the image, when the specific area is set on the display screen or the image, determining whether the point of gaze is within the specific area on the basis of a result of the detecting the position of the point of gaze, and when it is determined that the point of gaze is within the specific area, adjusting at least a mode in which the sound is output.

The above and other objects, features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 8 is a table representing exemplary data that is stored in a storage unit;

FIG. 9 is a table representing exemplary data that is stored in the storage unit;

FIG. 10 is a table representing exemplary data that is stored in the storage unit;

FIG. 26 is a flowchart illustrating another exemplary image sound output control process; and FIG. 27 is a diagram illustrating an electronic terminal that is another exemplary image sound output device according to the embodiment.

DETAILED DESCRIPTION

With reference to the drawings, an embodiment of the image sound output device, the image sound output method, and the image sound output program according to the present disclosure will be described below. Note that the embodiment does not limit the disclosure. The components of the embodiment include ones replaceable by and easy to those skilled in the art or ones substantially the same.

According to the following descriptions, a three-dimensional global coordinate system is set and the positional relationship among the components will be described below. A direction parallel with a first axis of a given plane serves as an X-axis direction, a direction parallel to a second-axis of a given plane orthogonal to the first axis serves as a Y-axis direction, and a direction parallel to a third axis orthogonal to the first axis and the second axis serves as a Z-axis direction. The given planes include X and Y planes.

Gaze Detection Device

Figure 1:
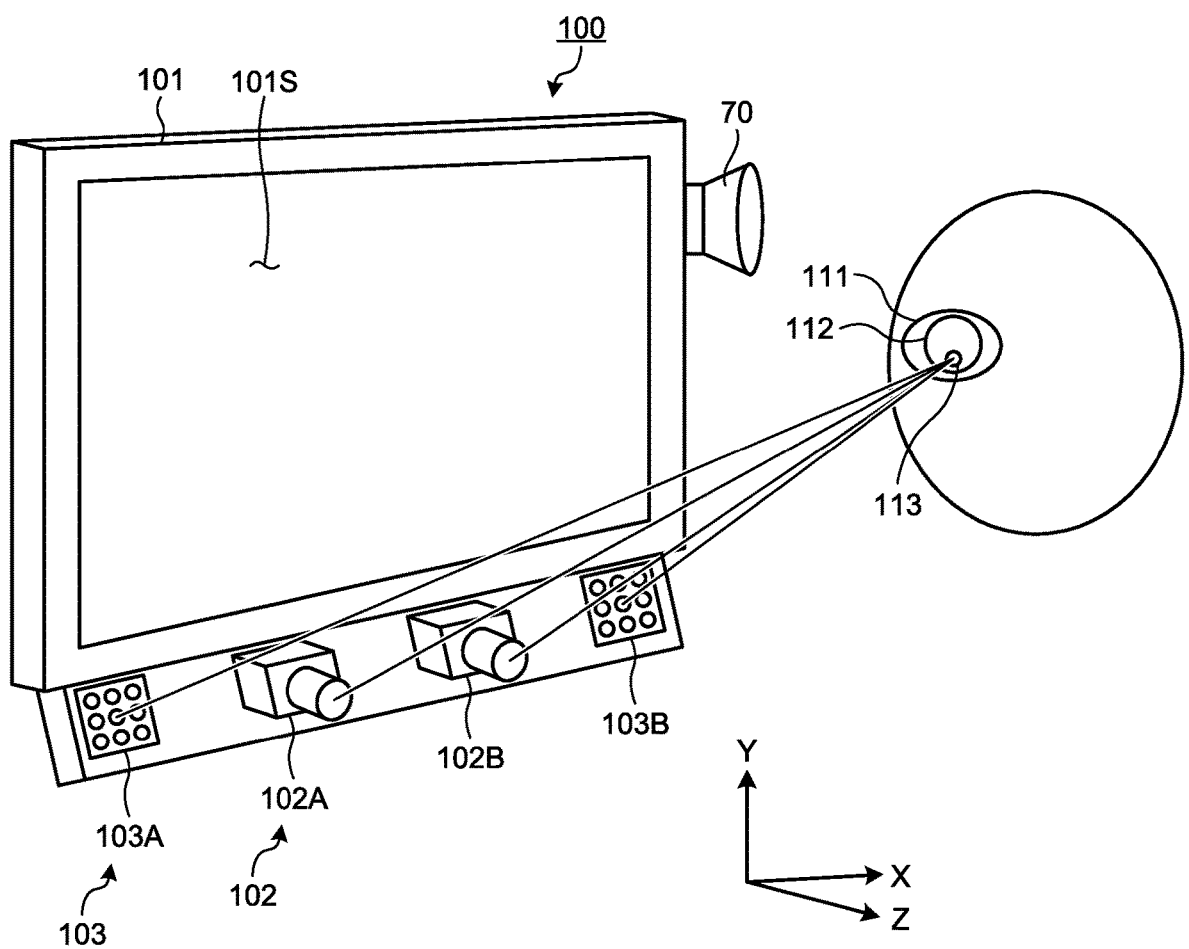
FIG. 1 is a perspective view schematically illustrating an exemplary gaze detection device that is an image sound output device according to an embodiment.

FIG. 1 is a perspective view schematically illustrating an exemplary gaze detection device 100 that is an image sound output device according to an embodiment. The gaze detection device 100 is used also as an evaluation device that evaluates a subject. As illustrated in FIG. 1, the gaze detection device 100 includes a display device 101, a sound output device 70, a stereo camera device 102 and an illumination device 103.

The display device 101 includes a flat panel display, such as a liquid crystal display (LCD) or an organic electroluminescence display (OLED). In the embodiment, the display device 101 includes a display screen 101S. The display screen 101S displays an image. The display screen 101S is substantially parallel to the X-Y plane. The X-axis direction is the horizontal direction of the display screen 101S, the Y-axis direction is the vertical direction of the display screen 101S, and the Z-axis direction is a depth direction orthogonal to the display screen 101S.

The sound output device 70, for example, includes a speaker and outputs sound for calling attention to the subject.

The stereo camera device 102 includes a first camera 102A and a second camera 102B. The stereo camera device 102 is arranged below the display screen 101S of the display device 101. The first camera 102A and the second camera 102B are arranged in the X-axis direction. The first camera 102A is arranged in the negative X-direction with respect to the second camera 102B. Each of the first camera 102A and the second camera 102B includes an infrared camera that includes, for example, an optical system capable of transmitting infrared light having a wavelength of 850 [nm] and an imaging device capable of receiving the infrared light.

The illumination device 103 includes a first light source 103A and a second light source 103B. The illumination device 103 is arranged below the display screen 101S of the display device 101. The first light source 103A and the second light source 103B are arranged in the X-axis direction. The first light source 103A is arranged in the negative X-direction with respect to the first camera 102A. The second light source 103B is arranged in the positive X-direction with respect to the second camera 102B. Each of the first light source 103A and the second light source 103B includes a light emitting diode (LED) light source that is able to emit near-infrared light having a wavelength of, for example, 850 [nm]. The first light source 103A and the second light source 103B may be arranged between the first camera 102A and the second camera 102B.

The illumination device 103 emits infrared light that is detection light to illuminate eyeballs 111 of the subject. The stereo camera device 102 images the eyeballs 111 with the second camera 102B when the detection light that is emitted from the first light source 103A is applied to the eyeballs 111 and images the eyeballs 111 with the first camera 102A when the detection light that is emitted from the second light source 103B is applied to the eyeballs 111.

A frame synchronization signal is output from at least one of the first camera 102A and the second camera 102B. The first light source 103A and the second light source 103B emit detection light according to the frame synchronization signal. The first camera 102A acquires image data about the eyeballs 111 when the detection light that is emitted from the second light source 103B is applied to the eyeballs 111. The second camera 102B acquires image data about the eyeballs 111 when the detection light that is emitted from the first light source 103A is applied to the eyeballs 111.

When the detection light is applied to the eyeball 111, part of the detection light reflects on a pupil 112 and the light from the pupils 112 is incident on the stereo camera device 102. When the detection light is applied to the eyeball 111, a corneal reflection image 113 that is a virtual image of the cornea is formed on the eyeball 111 and the light from the corneal reflection image 113 is incident on the stereo camera device 102.

Properly setting the relative positions among the first camera 102A, the second camera 102B, the first light source 103A and the second light source 103B lowers the intensity of the light incident on the stereo camera device 102 from the pupils 112 and increases the intensity of the light incident on the stereo camera device 102 from the corneal reflection images 113. In other words, the image of the pupils 112 that is acquired by the stereo camera device 102 has low luminance and the image of the corneal reflection images 113 has high luminance. The stereo camera device 102 is able to detect the positions of the pupils 112 and the positons of the corneal reflection images 113 on the basis of the luminance of the acquired images.

Figure 2:
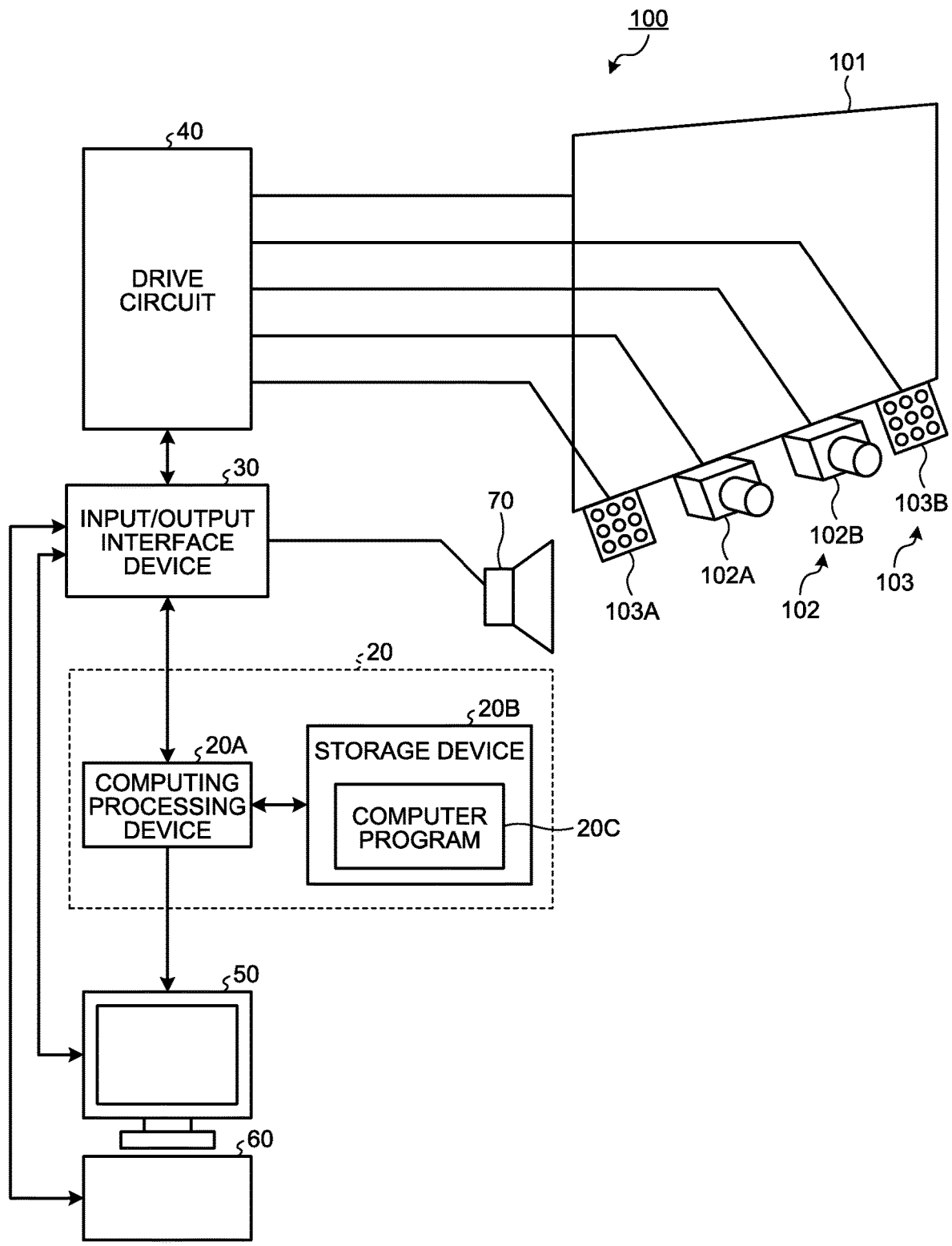
FIG. 2 is a diagram illustrating an exemplary hardware configuration of the gaze detection device according to the embodiment.

FIG. 2 is a diagram illustrating an exemplary hardware configuration of the gaze detection device 100 according to the embodiment. As illustrated in FIG. 2, the gaze detection device 100 includes the display device 101, the stereo camera device 102, the illumination device 103, a computer system 20, an input/output interface device 30, a drive circuit 40, an output device 50, an input device 60 and the sound output device 70.

The computer system 20, the drive circuit 40, the output device 50, the input device 60 and the sound output device 70 communicate data via the input/output interface device 30. The computer system 20 includes a computing processing device 20A and a storage device 20B. The computing processing device 20A includes a microprocessor, such as a central processing unit (CPU). The storage device 20B includes a memory, such as a read only memory (ROM) and a random access memory (RAM), or a storage. The computing processing device 20A performs arithmetic processing according to a computer program 20C that is stored in the storage device 20B.

The drive circuit 40 generates a drive signal and outputs the drive signal to the display device 101, the stereo camera device 102 and the illumination device 103. The drive circuit 40 supplies the image data about the eyeballs 111 that is acquired by the stereo camera device 102 to the computer system 20 via the input/output interface device 30.

The output device 50 includes a display device, such as a flat panel display. The output device 50 may include a printing device. The input device 60 is operated and thus generates input data. The input device 60 includes a keyboard or a mouse for computer systems. The input device 60 may include a touch sensor that is provided on the display screen of the output device 50, which is the screen serving as the display device.

In the embodiment, the display device 101 and the computer system 20 are devices independent of one another. The display device 101 and the computer system 20 may be integrated with each other. For example, when the gaze detection device 100 includes a tablet personal computer, the tablet personal computer may mount the computer system 20, the input/output interface device 30, the drive circuit 40, and the display device 101.

Figure 3:
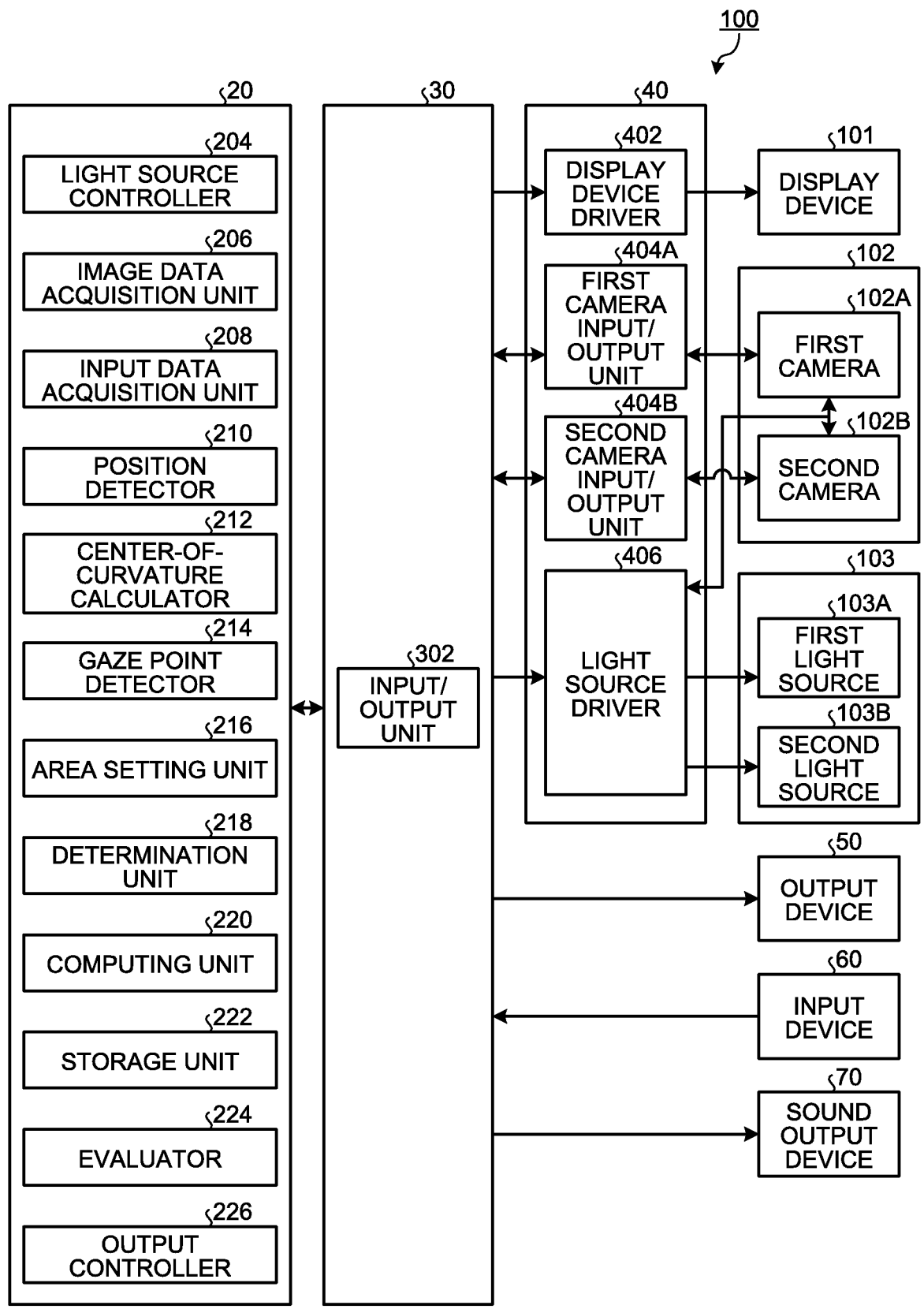
FIG. 3 is a functional block diagram illustrating an exemplary gaze detection device according to the embodiment.

FIG. 3 is a functional block diagram illustrating the exemplary gaze detection device 100 according to the embodiment. As illustrated in FIG. 3, the input/output interface device 30 includes an input/output unit 302. The drive circuit 40 includes a display device driver 402 that generates a drive signal for driving the display device 101 and outputs the drive signal to the display device 101; a first camera input/output unit 404A that generates a drive signal for driving the first camera 102A and outputs the drive signal to the first camera 102A; a second camera input/output unit 404B that generates a drive signal for driving the second camera 102B and outputs the drive signal to the second camera 102B; and a light source driver 406 that generates drive signals for driving the first light source 103A and the second light source 103B and outputs the drive signals to the first light source 103A and the second light source 103B. The first camera input/output unit 404A supplies the image data about the eyeballs 111 that is acquired by the first camera 102A to the computer system 20 via the input/output unit 302. The second camera input/output unit 404B supplies the image data about the eyeballs 111 that is acquired by the second camera 102B to the computer system 20 via the input/output unit 302.

The computer system 20 controls the gaze detection device 100. The computer system 20 includes a light source controller 204, an image data acquisition unit 206, an input data acquisition unit 208, a position detector 210, a center-of-curvature calculator 212, a gaze point detector 214, an area setting unit 216, a determination unit 218, a computing unit 220, a storage unit 222, an evaluator 224 and an output controller 226. The functions of the computer system 20 are implemented by the computing processing device 20A and the storage device 20B.

The light source controller 204 controls the light source driver 406 to control the operation mode of the first light source 103A and the second light source 103B. The light source controller 204 controls the first light source 103A and the second light source 103B such that the first light source 103A and the second light source 103B emit detection light at different sets of timing.

The image data acquisition unit 206 acquires the image data about the eyeballs 111 of the subject, which is acquired by the stereo camera device 102 including the first camera 102A and the second camera 102B, from the stereo camera device 102 via the input/output unit 302.

The input data acquisition unit 208 acquires the input data, which is generated by operating the input device 60, from the input device 60 via the input/output unit 302.

The position detector 210 detects positional data about the centers of the pupils on the basis of the image data about the eyeballs 111 that is acquired by the image data acquisition unit 206. The position detector 210 then detects positional data about the centers of the corneal reflection on the basis of the image data about the eyeballs 111 that is acquired by the image data acquisition unit 206. The centers of the pupils are the centers of the pupils 112. The centers of the corneal reflections are the centers of the corneal reflection images 113. The position detector 210 detects positional data about the center of the pupil and the positional data about the center of the corneal reflection with respect to each of the left and right eyeballs 111 of the subject.

The center-of-curvature calculator 212 calculates the positional data about the centers of the corneal curvatures of the eyeballs 111 on the basis of the image data about the eyeballs 111 that is acquired by the image data acquisition unit 206.

The gaze point detector 214 detects positional data about the point of gaze of the subject on the basis of the image data about the eyeballs 111 that is acquired by the image data acquisition unit 206. In the embodiment, the positional data about the point-of-gaze refers to positional data about the intersections each between a gaze vector of the subject that is defined by the three-dimensional global coordinate system and the display screen 101S of the display device 101. The gaze point detector 214 detects a gaze vector of each of the left and right eyeballs 111 of the subject on the basis of the positional data about the center of the pupil and the positional data about the center of the corneal curvature that are acquired from the image data about the eyeball 111. After the gaze vectors are detected, the gaze point detector 214 detects positional data about the points of gaze representing the intersections each between the gaze vector and the display screen 101S.

The area setting unit 216 sets a specific area on part of the display screen 101S or of the image. The area setting unit 216 is able to set a specific area on each image that is displayed on the display screen 101S. The area setting unit 216 is able to set specific areas in one or multiple areas in the image.

When a specific area is set on the display screen 101S or the image, the determination unit 218 determines whether the point of gaze is within the specific area on the basis of the positional data that is the result of detecting the position of the point of gaze and outputs data about the determination. The determination unit 218 determines whether the point of gaze is within the specific area, for example, at every given time. The given time may be, for example, a period (for example, every 50 [msec]) of the frame synchronization signal that is output from the first camera 102A and the second camera 102B.

The computing unit 220 includes a management timer that manages a time during which an image is displayed and a time during which a sound is output and a detection timer that detects the time elapsing from the display of the image on the display screen 101S. The computing unit 220 counts the number of times it is determined that the point of gaze is within the specific area. The computing unit 220 includes a counter that counts the number of times the determination about the specific area is made.

The evaluator 224 calculates evaluation data about the subject. The evaluation data is data to evaluate the subject on the basis of the result of the detection by the gaze point detector.

The storage unit 222 stores the image data about images to be displayed on the display screen 101S, sound data of sounds to be output from the sound output device 70, the determination data that is output from the determination unit 218, and the evaluation data that is output from the evaluator 224. The images to be displayed on the display screen 101S includes still images and moving images. The storage unit 222 stores multiple sets of image data and multiple sets of sound data. The storage unit 222 stores data indicating sets of timing of starting and ending display of the images and timing data that indicates sets of timing of starting and ending output of the sounds.

The storage unit 222 stores the image sound output program that causes a computer to execute a process including: causing a display screen to display an image; causing a sound output device to output a sound; detecting a position of a point of gaze of an observer observing the display screen; setting a specific area on part of the display screen or of the image; when the specific area is set on the display screen or the image, determining whether a point of gaze is within the specific area on the basis of a result of detecting the position of the point of gaze; and, when it is determined that the point of gaze is within the specific area, adjusting at least a mode in which a sound is output.

The output controller 226 outputs data to at least one of the display device 101, the output device 50 and the sound output device 70. In the embodiment, the output controller 226 causes the display screen 101S to display an image. The output controller 226 selects a given one of multiple sets of image data and causes the display screen 101S to display the image of the selected set of image data. The output controller 226 causes the sound output device 70 to output a sound. The output controller 226 selects a given one of multiple sets of sound data and causes the sound output device 70 to output the sound of the selected set of sound data.

When the determination unit 218 determines that the point of gaze is within the specific area, the output controller 226 adjusts at least the sound output mode in which the sound is output. Adjusting the sound output mode includes any one of stopping or ending output of the sound, restarting the output the sound from the mode in which the output is stopped, and adjusting the volume of the sound. Adjusting the sound output mode further includes switching the sound that is selected.

When the determination unit 218 determines that the point of gaze is within the specific area, the output controller 226 controls the timing of ending display of the image displayed on the display screen 101S. Controlling the timing of ending the display includes, for example, changing the timing of ending the display, which is the timing set in advance.

The output controller 226 may cause the display screen 101S or the output device 50 to display the position of the point of gaze of each of the left and right eyeballs 111 of the subject.

Figure 4:
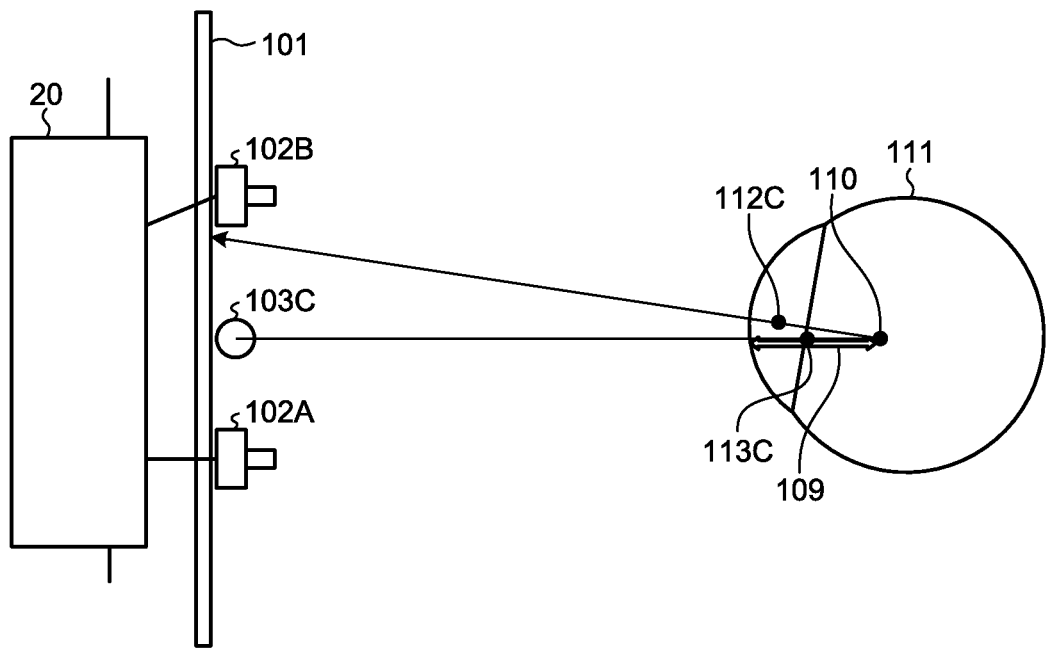
FIG. 4 is a schematic diagram for explaining a method of calculating positional data about the center of a corneal curvature according to the embodiment.
Figure 5:
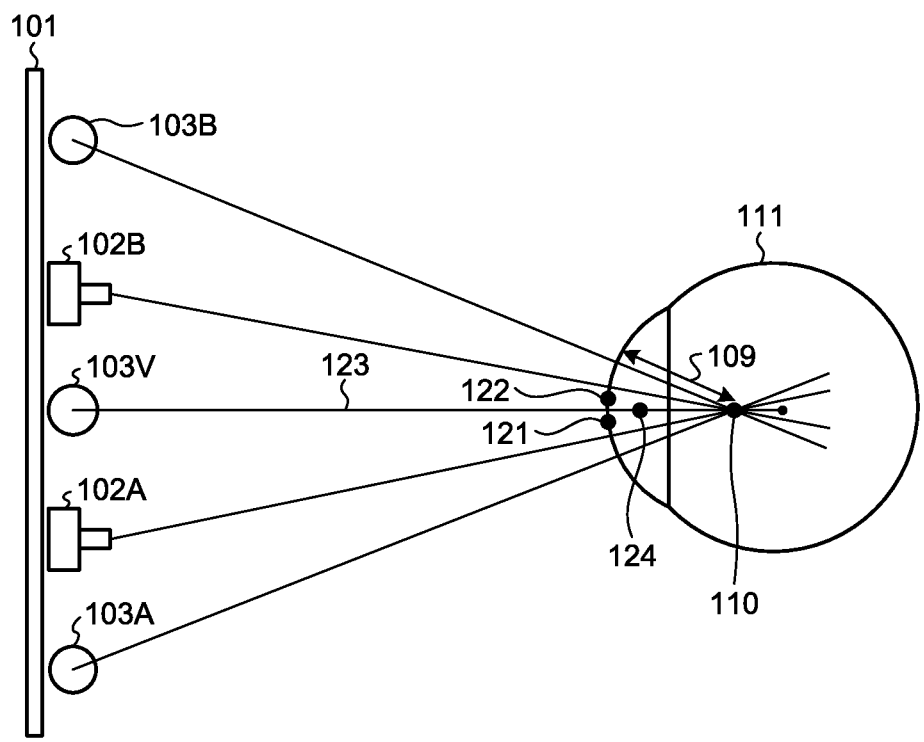
FIG. 5 is a schematic diagram for explaining the method of calculating positional data about the center of the corneal curvature according to the embodiment.

The overview of the process of the center-of-curvature calculator 212 according to the embodiment will be described. The center-of-curvature calculator 212 calculates positional data about the center of the corneal curvature of the eyeball 111 on the basis of the image data about the eyeballs 111. FIG. 4 and FIG. 5 are schematic diagrams for explaining the method of calculating positional data about a corneal curvature center 110 according to the embodiment. FIG. 4 illustrates an example where the eyeballs 111 are illuminated with a single light source 103C. FIG. 5 illustrates an example where the eyeballs 111 are illuminated with the first light source 103A and the second light source 103B.

First of all, the example illustrated in FIG. 4 will be described. The light source 103C is arranged between the first camera 102A and the second camera 102B. A pupil center 112C is the center of the pupil 112. A corneal reflection center 113C is the center of the corneal reflection image 113. In FIG. 4, the pupil center 112C represents the center of the pupil at the time when the eyeball 111 is illuminated with the single light source 103C. The corneal reflection center 113C represents the center of the corneal reflection at the time when the eyeball 111 is illuminated with the single light source 103C. The corneal reflection center 113C is on a straight line connecting the light source 103C and the corneal curvature center 110. The corneal reflection center 113C is positioned at a midpoint between the corneal surface and the corneal curvature center 110. A corneal curvature radius 109 is the distance between the corneal surface and the corneal curvature center 110. The positional data about the corneal reflection center 113C is detected by the stereo camera device 102. The corneal curvature center 110 is on a straight line connecting the light source 103C and the corneal reflection center 113C. The center-of-curvature calculator 212 calculates, as the positional data about the corneal curvature center 110, the positional data representing that the distance from the corneal reflection center 113C on the straight line is a given value. The given value is a value that is determined in advance from the value of a radius of curvature of a general cornea, etc., and is stored in the storage unit 222.

The example illustrated in FIG. 5 will be described. In the embodiment, the first camera 102A, the second light source 103B, the second camera 102B, and the first light source 103A are arranged at positions that are symmetrical with respect to a straight line passing through the mid-position between the first camera 102A and the second camera 102B. It is considered that there is a virtual light source 103V at the mid-position between the first camera 102A and the second camera 102B. A corneal reflection center 121 represents the center of the corneal reflection in an image of the eyeball 111 that is captured by the second camera 102B. A corneal reflection center 122 represents the center of the corneal reflection in an image of the eyeball 111 that is captured by the first camera 102A. A corneal reflection center 124 represents the center of the corneal reflection corresponding to the virtual light source 103V. The positional data about the corneal reflection center 124 is calculated based on positional data about the corneal reflection center 121 and positional data about the corneal reflection center 122, which are acquired by the stereo camera device 102. The stereo camera device 102 detects positional data about the corneal reflection center 121 and positional data about the corneal reflection center 122 in the three-dimensional local coordinate system that is defined by the stereo camera device 102. Camera calibration according to a stereo calibration method is performed on the stereo camera device 102 in advance to calculate a transformation parameter to transform the three-dimensional local coordinate system of the stereo camera device 102 into the three-dimensional global coordinate system. The transformation parameter is stored in the storage unit 222. The center-of-curvature calculator 212 transforms the positional data about the corneal reflection center 121 and the positional data about the corneal reflection center 122, which are acquired by the stereo camera device 102, into sets of positional data in the three-dimensional global coordinate system by using the transformation parameter. The center-of-curvature calculator 212 calculates positional data about the corneal reflection center 124 in the three-dimensional global coordinate system on the basis of the positional data about the corneal reflection center 121 and the positional data about the corneal reflection center 122, which are defined by the three-dimensional global coordinate system. The corneal curvature center 110 is on a straight line 123 connecting the virtual light source 103V and the corneal reflection center 124. The center-of-curvature calculator 212 calculates, as the positional data about the corneal curvature center 110, the positional data representing that the distance from the corneal reflection center 124 on the straight line 123 is a given value. The given value is a value that is determined in advance from the value of a radius of a curvature of a general cornea, etc., and is stored in the storage unit 222.

As described above, even when there are two light sources, the corneal curvature center 110 is calculated by using the same method as that for the case where there is a single light source.

The corneal curvature radius 109 is the distance between the corneal surface and the corneal curvature center 110. Accordingly, by calculating the positional data about the corneal surface and the positional data about the corneal curvature center 110, the corneal curvature radius 109 is calculated.

Figure 6:
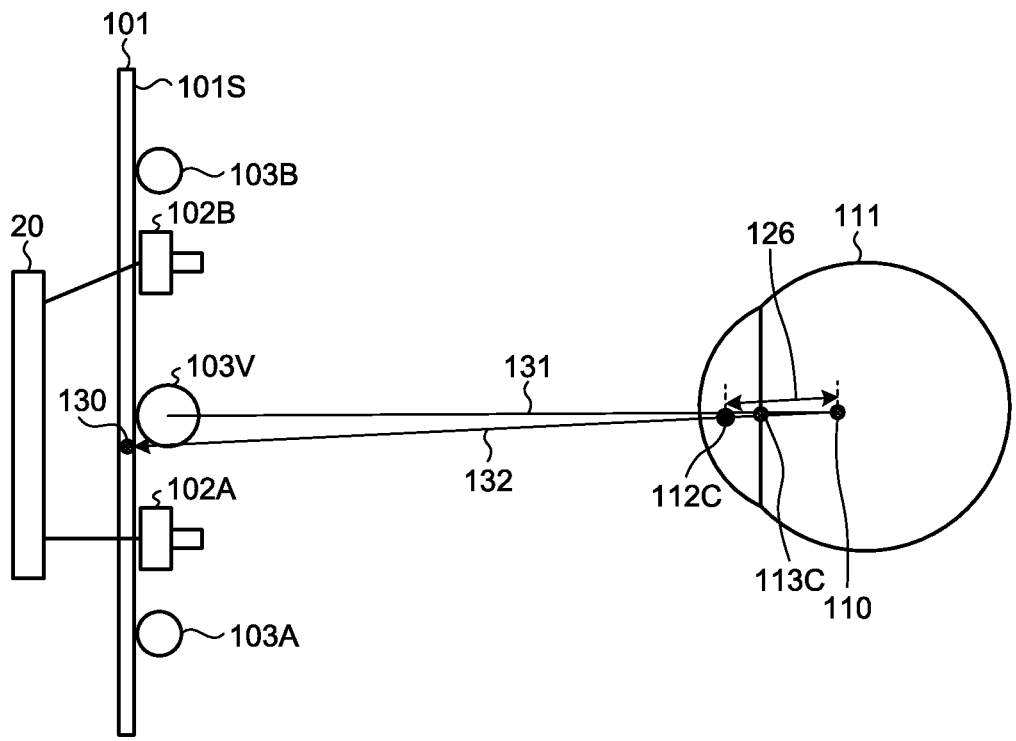
FIG. 6 is a schematic diagram for explaining an exemplary calibration process according to the embodiment.

An exemplary gaze detection method according to the embodiment will be described. FIG. 6 is a schematic diagram for explaining an exemplary calibration process according to the embodiment. In the calibration process, in order to cause the subject to have a gaze, a target position 130 is set. The target position 130 is defined in the three-dimensional global coordinate system. In the embodiment, the target position 130 is set, for example, at the center position of the display screen 101S of the display device 101. The target position 130 may be set at an end position of the display screen 101S. The output controller 226 displays a target image on the target position 130, which is set. A straight line 131 is a straight line connecting the virtual light source 103V and the corneal reflection center 113C. A straight line 132 is a straight line connecting the target position 130 and the pupil center 112C. The corneal curvature center 110 is the intersection between the straight line 131 and the straight line 132. The center-of-curvature calculator 212 is able to calculate positional data about the corneal curvature center 110 on the basis of positional data about the virtual light source 103V, positional data about the target position 130, positional data about the pupil center 112C, and the positional data about the corneal reflection center 113C.

Figure 7:
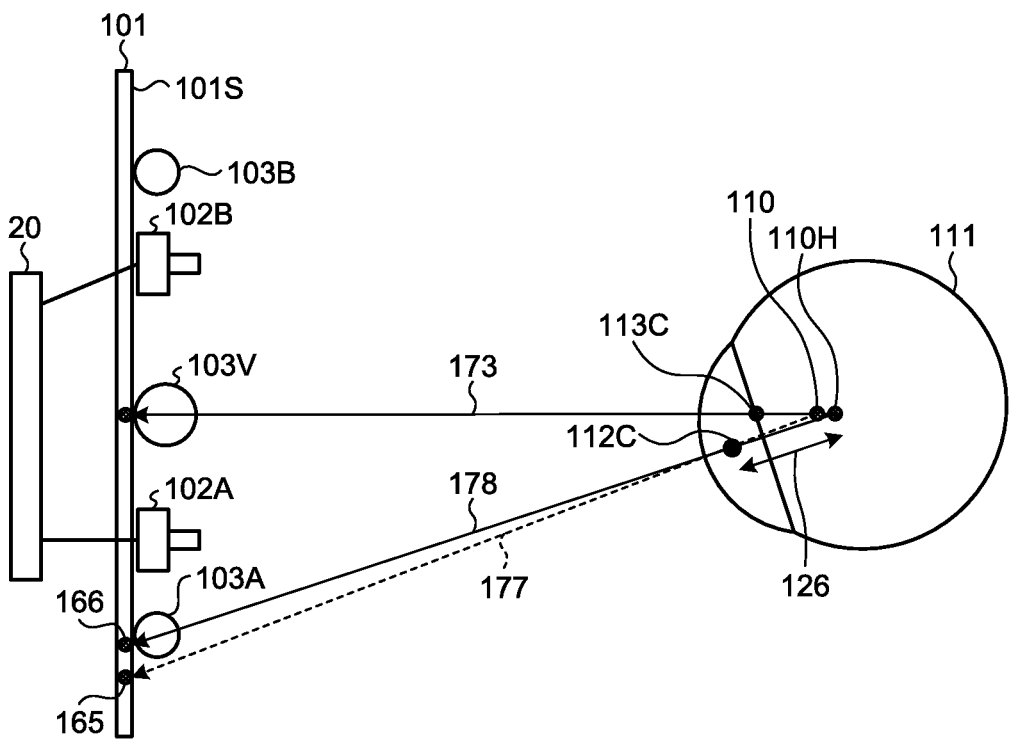
FIG. 7 is a schematic diagram for explaining an exemplary point-of-gaze detection process according to the embodiment.

A point-of-gaze detection process will be described. The point-of-gaze detection process is performed after the calibration process. The gaze point detector 214 calculates a gaze vector of the subject and positional data about the point of gaze on the basis of the image data about the eyes 111. FIG. 7 is a schematic diagram for explaining the exemplary point-of-gaze detection process according to the embodiment. In FIG. 7, a gaze point 165 represents a point of gaze that is calculated from a corneal curvature center that is calculated by using the value of a radius of a general curvature. A gaze point 166 represents a point of gaze that is calculated from the center of the corneal curvature that is calculated by using a distance 126 that is calculated in the calibration process. The pupil center 112C represents the center of the pupil that is calculated in the calibration process. The corneal reflection center 113C represents the center of the corneal reflection that is calculated in the calibration process. A straight line 173 is a straight line connecting the virtual light source 103V and the corneal reflection center 113C. The corneal curvature center 110 is the position of the center of the corneal curvature that is calculated from the value of a radius of a general curvature. The distance 126 is the distance between the pupil center 112C and the corneal curvature center 110 that is calculated by the calibration process. A corneal curvature center 110H represents the position of the corneal curvature center after correction of the corneal curvature center 110 by using the distance 126. The corneal curvature center 110H is calculated from the fact that the corneal curvature center 110 is on the straight line 173 and the distance between the pupil center 112C and the corneal curvature center 110 is the distance 126. Accordingly, a line-of-sight 177 that is calculated in the case where the value of the curvature of the general radius is used is corrected to a line-of-sight 178. The point of gaze on the display screen 101S of the display device 101 is corrected from the gaze point 165 to the gaze point 166.

Image Sound Output Method

The image sound output method according to the embodiment will be described. FIG. 8 is a table representing exemplary data that is stored in the storage unit 222. FIG. 8 represents exemplary image data. As represented in FIG. 8, with respect to sets of image data of multiple images to be displayed on the display screen 101S of the display device 101, the order in which the images are displayed, image numbers to identify the sets of image data, and reproduction times during which the images are reproduced, respectively, are stored in association with one another in the storage unit 222. The output controller 226 causes the display screen 101S to display images 1 to 6 in turns for the corresponding reproduction times, respectively, according to the data stored in the storage unit 222.

For example, first of all, the output controller 226 starts display of the image 1 and ends the display of the image 1 after the elapse of a time t1. The output controller 226 starts display of the image 2 after ending the display of the image 1 and ends the display of the image 2 after the elapse of a time 2 from the start of the display. The output controller 226 performs the process repeatedly on the images 3 to 6 and ends the process after ending the display of the image 6.

FIG. 9 is a table representing exemplary data that is stored in the storage unit 222. FIG. 9 represents exemplary timing data representing the timing of starting and ending output of sound data. As represented in FIG. 9, each set of sound data is stored as timing data in the storage unit 222 in association with an output start setting, an output end setting, and the number of times of output. The output start setting represents the content serving as a trigger to start output of sound data. The output end setting represents the content serving as a trigger to end output of the sound data. The number of times of output represents the number of times the sound data is output. For example, when the number of times of output is multiple times, that is, twice or more, it is indicated that the sound data is to be output repeatedly for multiple times.

For example, when two seconds elapse from the start of the display of the image 1, the output controller 226 starts output of a sound 1. The output controller 226 ends the output of the sound 1 when ten seconds elapse from the start of the output of the sound 1. When the output controller 226 ends the output of the sound 1, the output controller 226 ends the process of the sound 1 without repetition.

The output controller 226 starts the output of a sound 2 simultaneously with the start of the display of the image 2. The output controller 226 ends the output of the sound 2 when five seconds elapse from the start of display of the image 3 after the display of the image 2 is ended. When the output controller 226 ends the output of the sound 2, the output controller 226 ends the process of the sound 2 without repetition.

FIG. 10 is a table representing exemplary data that is stored in the storage unit 222. FIG. 10 represents exemplary volume data representing the volume of each sound. As represented in FIG. 10, each set of sound data is stored in the storage unit 222 in association with the time elapsing from the start of the output and the volume, which is set. The output controller 226 keeps the volume at 50 until ten seconds elapses from the start of the output of the sound 1, keeps the volume at 20 after ten seconds elapse, and keeps the volume at 50 after 20 seconds elapse, and keeps the volume at 20 after 30 seconds elapse. Similarly, the output controller 226 keeps the volume at 0 until 0.5 second elapses from the start of the output of the sound 2, keeps the volume at 10 after 0.5 second elapses, keeps the volume at 20 after one second elapses, and keeps the volume at 30 after 1.5 second elapses.

Figure 11:
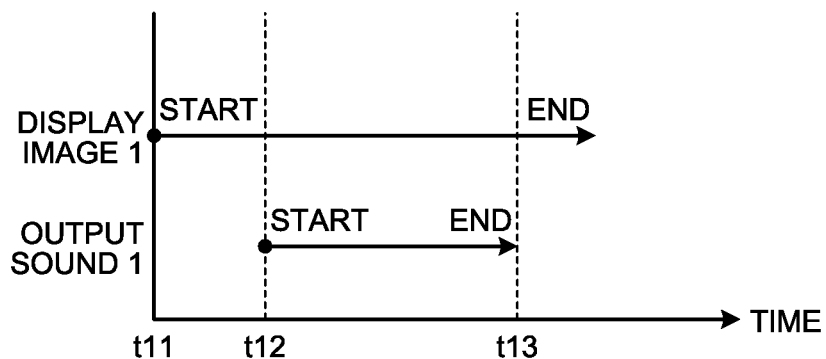
FIG. 11 is a timing chart indicating the timing of starting and ending display of an image and the timing of starting and ending output of a sound in association with each other.
Figure 15:
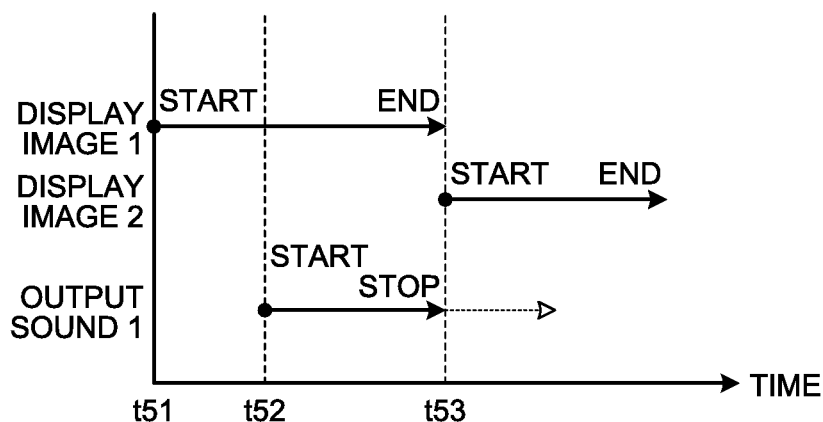
FIG. 15 is a timing chart indicating the sets of timing of starting and ending display of images and the timing of starting and ending output of a sound in association with each other.
Figure 16:
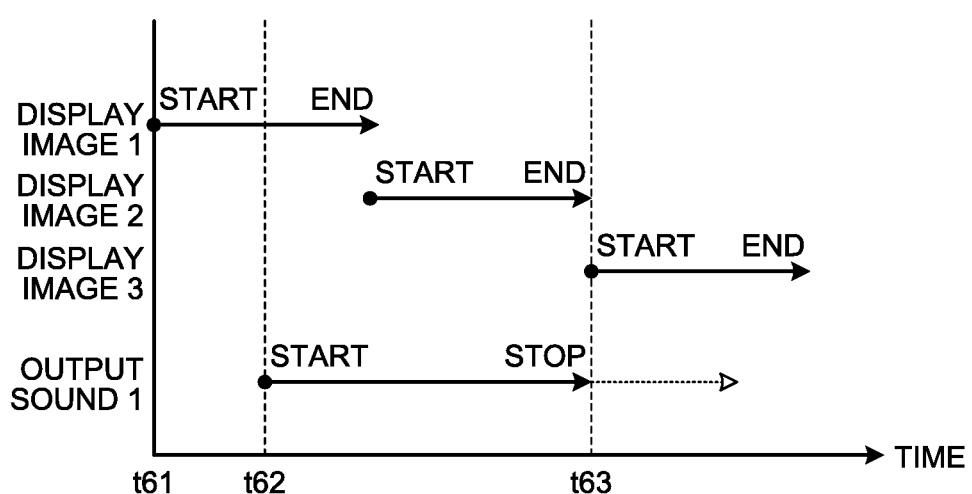
FIG. 16 is a timing chart indicating the sets of timing of starting and ending display of images and the timing of starting and ending output of a sound in association with each other.
Figure 17:
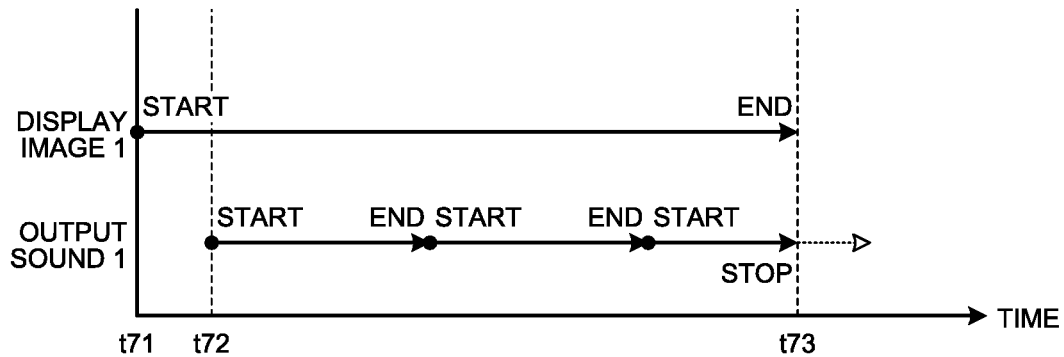
FIG. 17 is a timing chart indicating the timing of starting and ending display of an image and the timing of starting and ending output of a sound in association with each other.

FIGS. 11 to 17 are timing charts representing the sets of timing of starting and ending display of images and the sets of timing of starting and ending output of sounds in association with each other. Each of the patterns illustrated in FIGS. 11 and 17 are, for example, set in advance and stored in the storage unit 222. Each of the following diagrams illustrates the exemplary images 1 to 3 as an exemplary case where multiple images are displayed in turns; however, the images are not limited thereto, and other images may be displayed. The sound 1 will be described as exemplary sound; however, the sound is not limited thereto, and another sound may be output.

The timing chart of FIG. 11 represents the case where a time t12 representing the timing of starting output of the sound 1 is "the time of the time point at which the given time elapses from the time t11 to start display of the image 1" and a time t13 representing the timing of ending output of the sound 1 is "the time point at which the sound 1 is output to the end". In this case, it is possible to provide a time for the subject to focus on the image.

Figure 12:
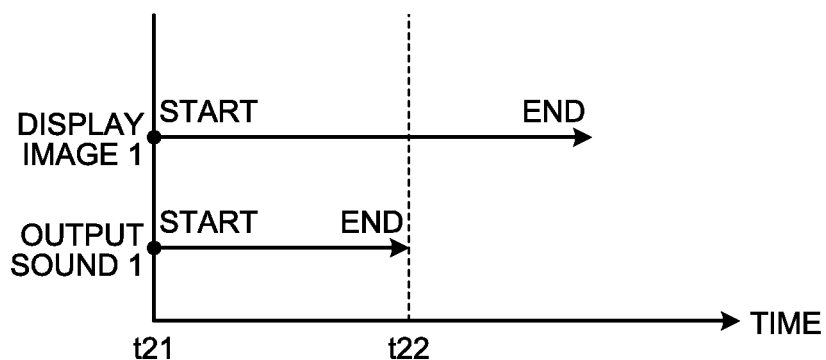
FIG. 12 is a timing chart indicating the timing of starting and ending display of an image and the timing of starting and ending output of a sound in association with each other.

The timing chart of FIG. 12 represents the case where a time t21 representing the timing of starting output of the sound 1 is "simultaneous to the time to start display of the image 1" and a time t22 representing the timing of ending output of the sound 1 is "the time point at which the sound 1 is output to the end".

Figure 13:
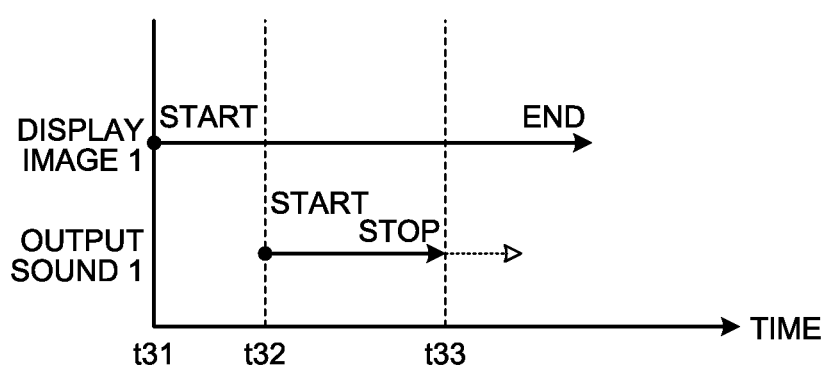
FIG. 13 is a timing chart indicating the timing of starting and ending display of an image and the timing of starting and ending output of a sound in association with each other.

The timing chart of FIG. 13 represents the case where a time t32 representing the timing of starting output of the sound 1 is "the time of the time point at which a given time elapses from a time t31 to start display of the image 1" and a time t33 representing the timing of ending output of the sound 1 is "the time of the time point at which a given time elapses from the time t32 to start the output". In this case, the output ends even when the sound 1 is in the middle.

Figure 14:
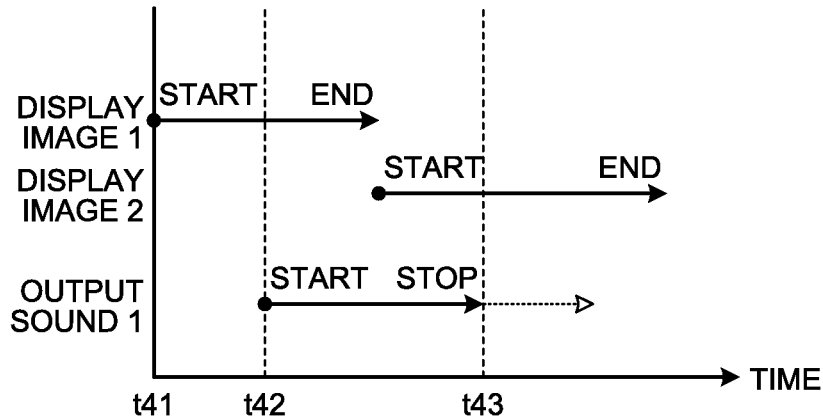
FIG. 14 is a timing chart indicating the sets of timing of starting and ending display of images and the timing of starting and ending output of a sound in association with each other.

The timing chart of FIG. 14 represents the exemplary case where the sound 1 is output over a display period for multiple images (the image 1 and the image 2). In this case, a time t42 representing the timing of starting output of the sound 1 is "the time of the time point at which a given time elapses from a time t41 to start display of the image 1" and a time t43 representing the timing of ending output of the sound 1 is "the time of the time point at which a given time elapses from the time to start display of the image 2". In this case, the output ends even when the sound 1 is in the middle.

According to the timing chart of FIG. 15, a time t52 representing the timing of starting output of the sound 1 is "the time of a time point at which a given time elapses from a time t51 to start display of the image 1" and a time t53 representing the timing of ending output of the sound 1 is "the time to start display of the image 2". In this case, the output ends even when the sound 1 is in the middle.

According to the timing chart of FIG. 16, a time t62 representing the timing of starting output of the sound 1 is "the time of a time point at which a given time elapses from a time t61 to start display of the image 1" and a time t63 representing the timing of ending output of the sound 1 is "the time to end the display of the image 2 (or the time to start display of the image 3)". In this case, the output ends even when the sound 1 is in the middle.

The timing chart of FIG. 17 represents the exemplary case where the sound 1 is output repeatedly for multiple times. In this case, a time t72 representing the timing of starting output of the sound 1 is "the time of a time point at which a given time elapses from a time t71 to start display of the image 1" and a time t73 representing the timing of ending output of the sound 1 is "the time to end the display of the image 1". In this case, the output ends even when the sound 1 is in the middle.

The above-described relationships between the sets of timing of displaying images and the sets of timing of displaying the sounds are examples only. It is thus possible to set other patterns different from the above-described patterns.

Figure 18:
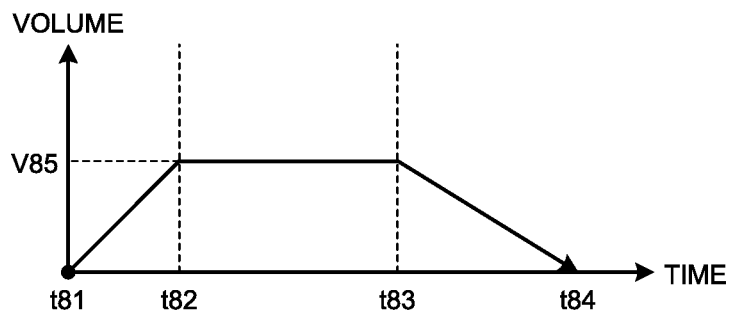
FIG. 18 is a timing chart indicating the timing of starting and ending output of a sound and the volume in association with each other.
Figure 19:
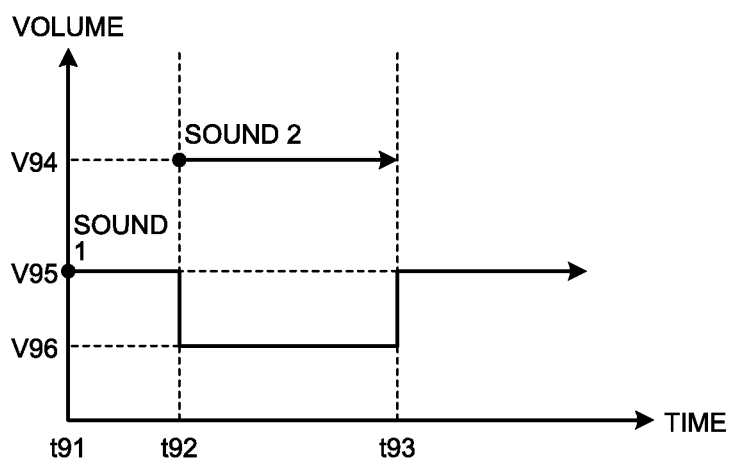
FIG. 19 is a timing chart indicating the sets of timing of starting and ending output of sounds and the volume in association with each other.

FIGS. 18 and 19 are timing charts representing the sets of timing of starting and ending to output sounds and the volume in association with each other. Each of the patterns represented in FIG. 18 and FIG. 19 is, for example, set in advance and stored in the storage unit 222.

According to the timing chart of FIG. 18, the volume at the time t81 to start output of the sound is 0 and the volume at the time t82 is V85. The volume is increased constantly between the time t81 and the time t82. The volume is maintained at V85 between the time t82 and the time t83. The volume is reduced constantly from V85 to 0 between the time t83 to a time t84.

According to the timing chart of FIG. 19, the volume at a time t91 to stat outputting the sound 1 is at V95 and the volume reduces to V96 lower than V95 at a time t92 and is maintained until the time t93. At and after the time t93, the volume is at V95 again. The sound 2 is output at V94 that is a volume larger than V95 between the time t92 and the time t93 when the volume of the sound 1 reduces. As described above, it is possible to output different sounds simultaneously.

The above-described timing of changing the volume is an example. It is thus possible to set another pattern different from the above-described pattern.

Figure 20:
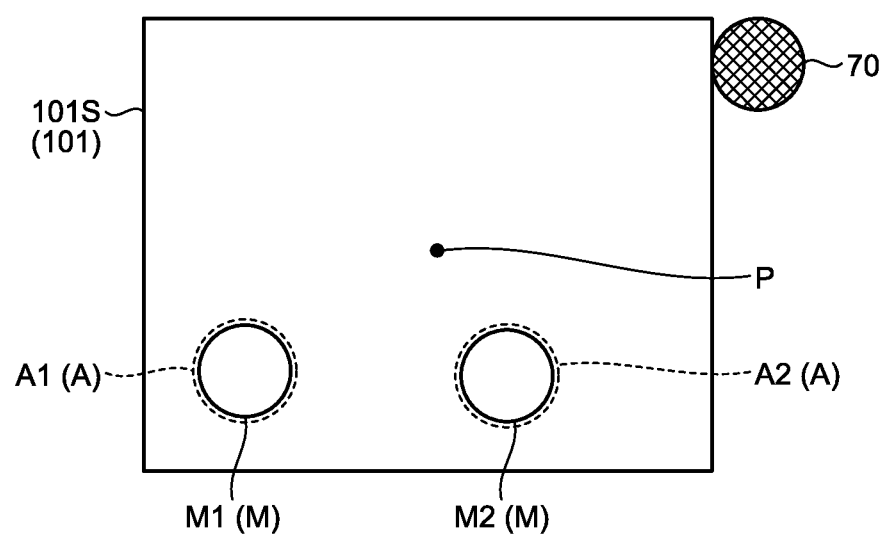
FIG. 20 is a diagram illustrating an exemplary image that is displayed on a display screen of a display device.

FIG. 20 is a diagram illustrating an exemplary image that is displayed on the display screen 101S of the display device 101. As illustrated in FIG. 20, the area setting unit 216 sets a specific area A on part of the display screen 101S or of the image. The area setting unit 216 is able to set the specific area A in one or more spots on the display screen 101S or the image. In the embodiment, for example, the specific area A is set in two spots; however, the embodiment is not limited thereto. When two specific areas A are distinguished from one another below, they may be referred to as specific areas A1 and A2. Each of the specific areas A is for example, circular; however, the embodiment is not limited thereto, and each of the specific areas A may be rectangular or may have another shape and the different specific areas A may have different shapes and sizes. When setting multiple specific areas A, the area setting unit 216 sets the specific areas A, for example, on the display screen 101S distantly from one another.

On the image displayed on the display screen 101S, the output controller 226 displays objects M respectively in positions and areas corresponding to the specific areas A. In the embodiment, for example, two objects M are displayed as the multiple objects M. When the two objects M are referred to, the objet M displayed in the specific area A1 may be referred to as an object M1 and the objet M displayed in the specific area A2 may be referred to as an object M2 below. For example, a pattern, etc., may be formed in the object M. The shape of the object M may match or different from the shape of the specific area A.

FIG. 20 illustrates an exemplary point of gaze that is displayed by the output controller 226 as the result of measurement on the display screen 101S. The output controller 226 prevents point of gaze from being displayed while the point of gaze of the subject is being detected. The positional data about the point of gaze is detected, for example, according to the period (for example, every 50 [msec]) of the frame synchronization signals that are output from the first camera 102A and the second camera 102B. The first camera 102A and the second camera 102B capture images in synchronization with each other.

When the specific area A is set on the display screen 101S, the determination unit 218 determines whether the point of gaze is within the specific area A on the basis of the positional data that is the result of the detection of the position of the point of gaze and outputs data about the detection. The determination unit 218 determines whether the point of gaze is within the specific area at every given time. The given time may be, for example, the period (for example, 50 [msec]) of the frame synchronization signals that are output from the first camera 102A and the second camera 102B.

When the determination unit 218 determines that the point of gaze is within the specific area A, the output controller 226 adjusts at least the sound output mode. Adjusting the sound output mode includes any one of stopping or ending to output the sound, restarting output of the sound from the mode in which the output is stopped, and adjusting the volume of the sound. Adjusting the sound output mode includes switching the sound that is selected.

When the determination unit 218 determines that the point of gaze is within the specific area A, the output controller 226 controls the timing of ending display of the image displayed on the display screen 101S. Controlling the timing of ending the display includes, for example, changing the pre-set timing of ending the display.

When multiple specific areas A are set, the output controller 226 is able to change the content of the control on the timing of adjusting the sound output mode and of ending display of the image according to within which of the specific areas A the point of gaze of the subject is. For example, when the point of gaze of the subject is within the specific area A1, it is possible to enable both adjustment of the sound output mode and control on the timing of ending display of the image. When the point of gaze of the subject is within the specific area A2, it is possible to enable only adjustment of the sound output mode.

For example, as for other exemplary setting, when the point of gaze of the subject is within the specific area A1, ending the sound output may be enabled as the adjustment of the sound output mode. When the point of gaze of the subject is within the specific area A2, switching the sound to be output to another sound may be enabled as the adjustment of the sound output mode.

The content of the adjustment of the sound output mode and the content of the combination of the adjustment of the sound output mode and the control on the timing of ending display of the image, which are described above, are an example only and thus the embodiment is not limited thereto. According to within which of the specific areas A the point of gaze is, a setting may be made to enable different content of the adjustment of the sound output mode and a setting may be made to enable different content of the combination between the adjustment of the sound output mode and the control on the timing of ending display of the image.

Figure 21:
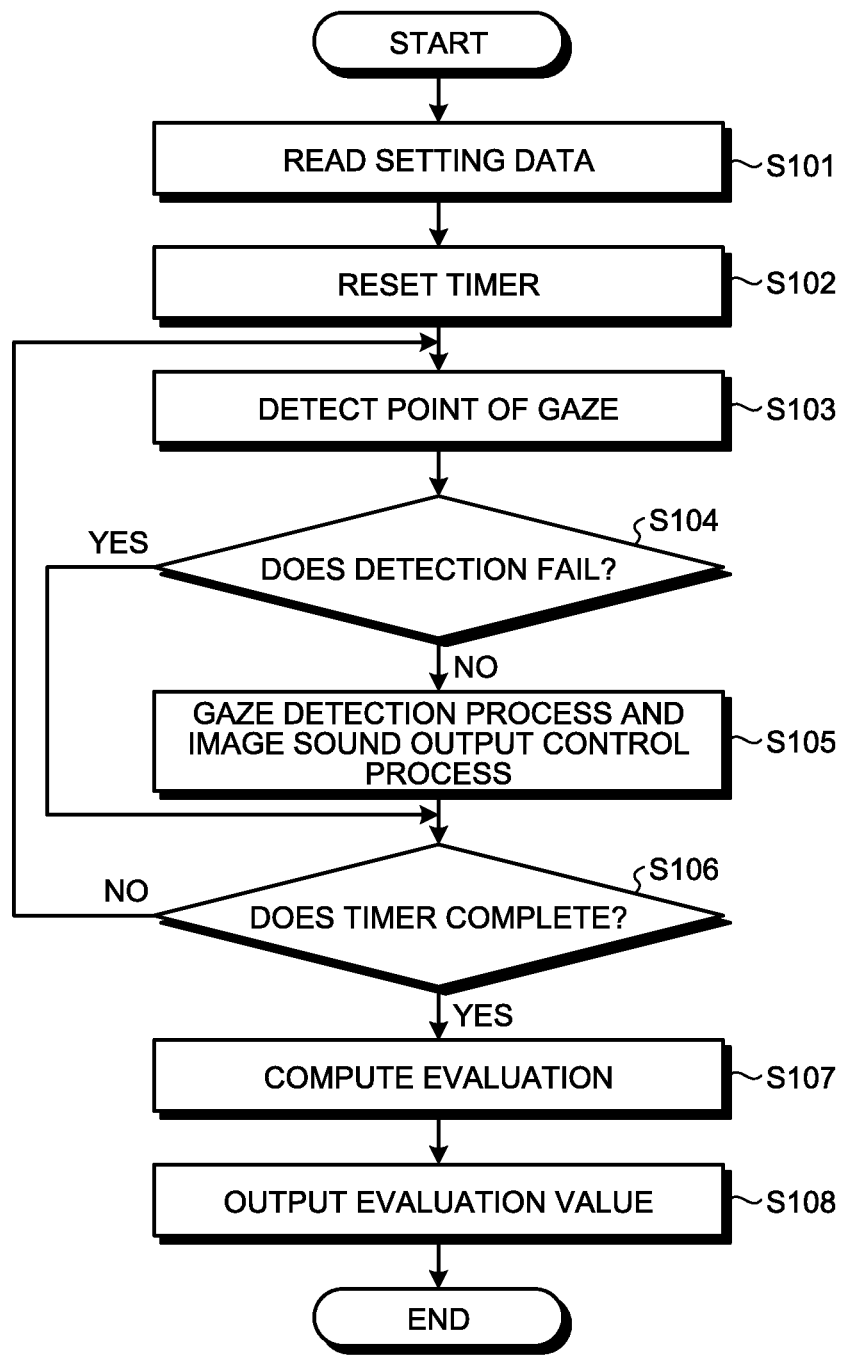
FIG. 21 is a flowchart illustrating operations of the gaze detection device.

Exemplary operations of the gaze detection device 100 according to the embodiment will be described with reference to FIG. 21. FIG. 21 is a flowchart illustrating the operations of the gaze detection device 100. First of all, the output controller 226 reads each of the sets of data represented in FIGS. 8 to 19, that is, the setting data for images and sounds, the setting data for volume control, timing data, etc., from the storage unit 222 (step S101).

The computing unit 220 then resets the management timer for managing the times during each of which an image is displayed and the times during each of which a sound is output (step S102). In the state where an image displayed on the display device 101 is represented to a subject, the gaze point detector 214 starts the point-of-gaze detection process to detect positional data about the point of gaze of the subject on the display screen 101S of the display device 101 at every given sampling period (for example, 50 [ms]) (step S103).

When the positional data is detected (NO at step S104), the display screen 101S is caused to display an image and the sound output device 70 is caused to output a sound to perform a given gaze detection process and, according to the result of gaze detection, an image sound output control process is performed (step S105). The gaze detection process and the image sound output control process at step S105 will be described below. When the process at step S105 ends or the positional data is not detected at step S104 (YES at step S104), it is determined whether the management timer reaches a given time (step S106). When the management timer does not reach the given time (NO at step S106), the process at and after step S103 is performed repeatedly. When the management timer reaches the given time (YES at step S106), point-of-gaze data that is obtained through the gaze detection process is evaluated (step S107) and an evaluation value is output (step S108).

Figure 22:
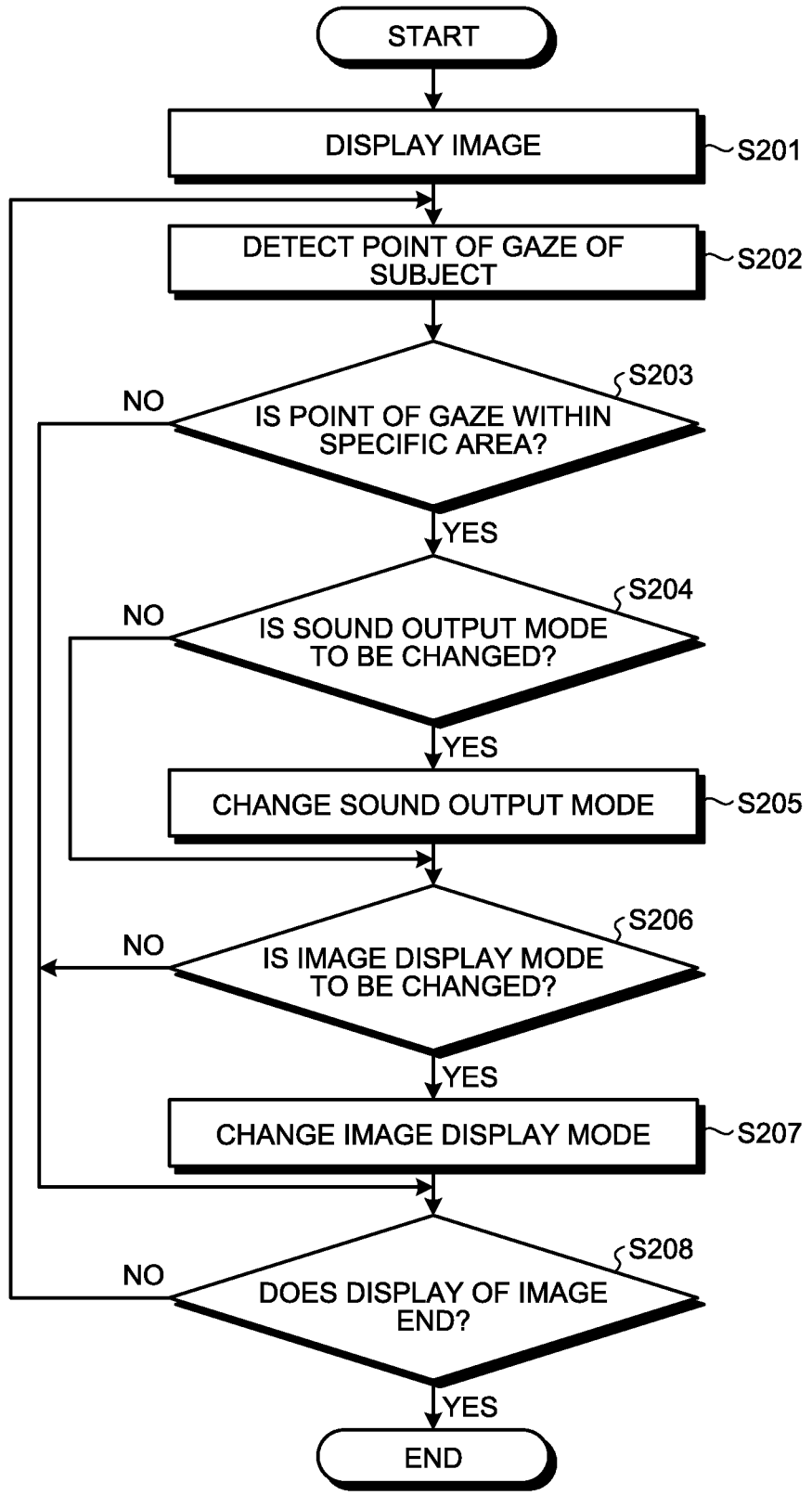
FIG. 22 is a flowchart illustrating an exemplary gaze detection process and an exemplary image sound output control process according to the embodiment.

The gaze detection process and the image sound output control process at step S105 will be described. In the gaze detection process and the image sound output control process at step S105, the gaze point detector 214 performs the gaze detection process and the output controller 226 performs the image sound output control process according to the embodiment. FIG. 22 is a flowchart illustrating an exemplary gaze detection process and an exemplary image sound output control process according to the embodiment. The output controller 226 causes the display screen 101S to display an image for gaze detection (step S201). With the image being displayed on the display screen 101S, the gaze point detector 214 detects positional data about the point of gaze of the subject (step S202).

The determination unit 218 determines whether the point of gaze is within the specific area A (step S203). When it is determined that the point of gaze is within the specific area A, the output controller 226 determines whether to change the sound output mode in the sound output device 70 (step S204). When the output controller 226 determines to change the sound output mode (YES at step S204), the output controller 226 changes the sound output mode in the sound output device 70 (step S205). When the output controller 226 changes the sound output mode, the output controller 226 determines whether to change the image display mode (step S206). When the output controller 226 determines to change the image display mode (YES at step S206), the output controller 226 changes the image display mode (step S207).

After the process at step S207 is performed or when the NO process at step S203, the NO process at step S204 or the NO process at step S206 is performed, the output controller 226 determines whether the display of the image ends (step S208). On determining that the display of the image ends (YES at step S208), the output controller 226 ends the process. On determining that display of the image does not end (NO at step S208), the output controller 226 causes the process at and after step S202 to be performed repeatedly.

Figure 23:
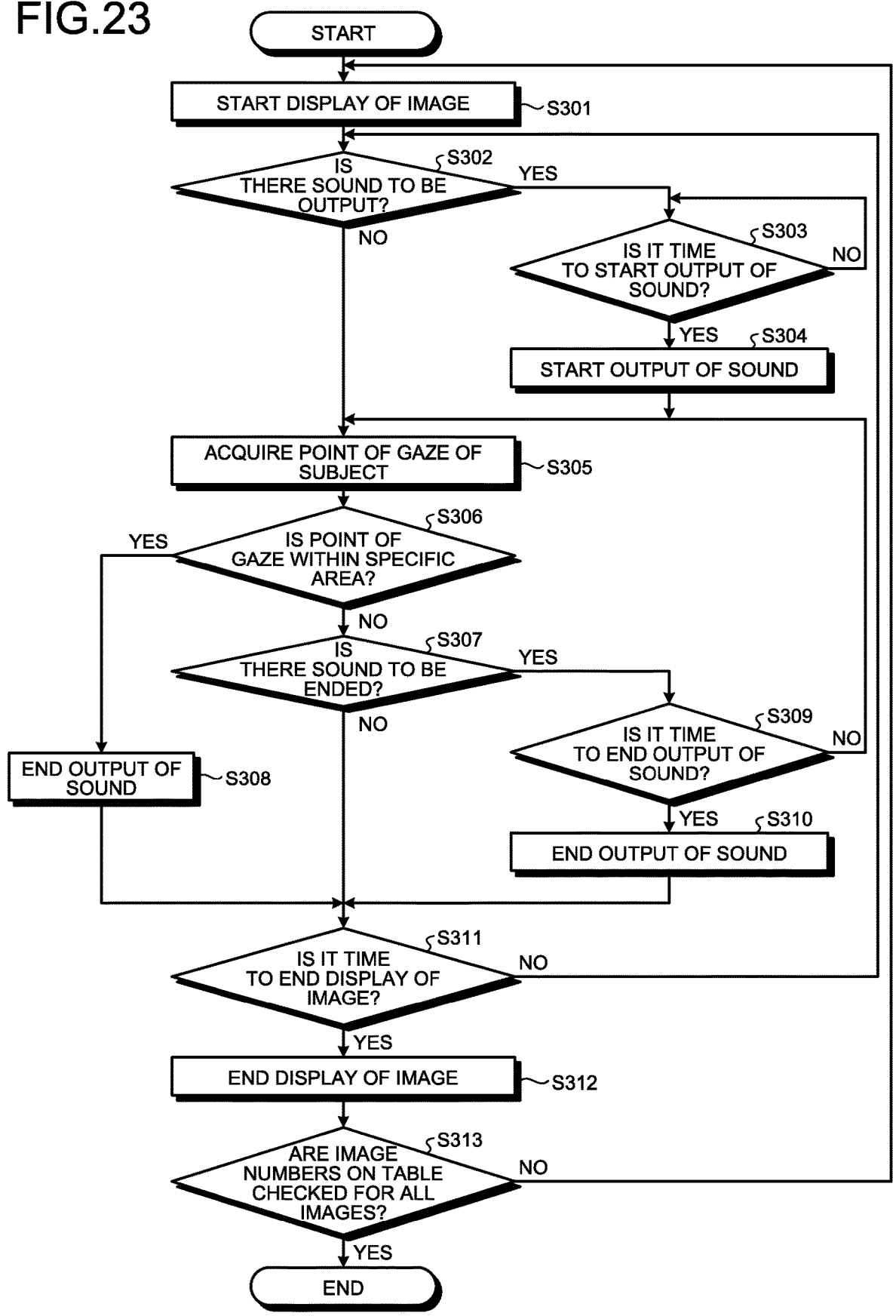
FIG. 23 is a flowchart illustrating an exemplary image sound output control process.

The case where, in the gaze detection process and the image sound output control process at step S105, the sound output mode and the image display mode are changed by the image sound output control process according to the embodiment will be specifically described below. FIG. 23 is a flowchart illustrating the exemplary image sound output control process. FIG. 23 illustrates the exemplary case where the sound output ends according to the positional data about the point of gaze of the subject.

First of all, the output controller 226 causes the display device 101S to display an image for gaze detection (step S301). At step S301, the output controller 226 causes the display device 101S to display a given image from among the images 1 to 6 that are stored in the storage unit 222. The area setting unit 216 sets the specific area A on part of the display screen 101S or the given image from among the images 1 to 6. The computing unit 220 detects the time elapsing from the display of the image 1 by using the detection timer.

The output controller 226 then determines whether there is a sound to be output from the sound output device 70 (step S302). At step S302, the output controller 226 detects whether there is, for example, a sound that is stored in association with "the image 1" from among the sounds that are stored in the storage unit 222.

On determining that there is a sound to be output, the output controller 226 determines whether the time to start output of the sound is reached (step S303). When the time to start output of the sound is not reached (NO at step S303), the output controller 226 repeats the determination at step S303 until the time to start the output is reached. On determining that the time to start output of the sound is reached (YES at step S303), the output controller 226 starts the output of the sound (step S304).

After the process of NO at step S302 or the process at step S304 is performed, the gaze point detector 214 acquires the positional data about the point of gaze of the subject (step S305). At step S305, the gaze point detector 214 detects positional data about the point of gaze of the subject on the display screen 101S of the display device 101 at every given sampling period (for example, 50 [msec]).

The determination unit 218 determines whether the point of gaze of the subject is within the specific area A in the image displayed on the display screen 101S (step S306). At step S306, the determination unit 218 determines whether the point of gaze is within the specific area A at every given time. The given time may be, for example, the period (for example, every 50 [msec]) of frame synchronization signals that are output from the first camera 102A and the second camera 102B.

When it is determined that the point of gaze is within the specific area A (YES at step S306), the output controller 226 changes the sound output mode. In this case, the output controller 226, for example, ends the output of the sound (step S308). At step S308, for example, even at the timing not in the timing data stored in the storage unit 222, the output controller 226 ends the output of the sound by using the result of the determination by the determination unit 218 as a trigger. In the same manner, the sound output may be stopped (suspended).

At step S306, when it is determined that the point of gaze of the subject is not within the specific area A, the output controller 226 determines whether there is a sound to be ended (step S307). At step S307, the output controller 226 determines whether a sound is output at the time of step S307 and, when a sound is output, determines that there is a sound to be ended. When no sound is output at the time of step S307, the output controller 226 determines that there is no sound to be output.

On determining that there is a sound to be ended at step S307, the output controller 226 determines whether it is time to end the output of the sound (step S309). The time to end the output is, for example, the time to end the sound in the timing chart (see FIGS. 11 to 17) that is stored in the storage unit 222. On determining that it is not time to end the output of the sound (NO at step S309), the output controller 226 repeats the determination at step S309 until the time to end the output is reached. On determining that the time to end the output of the sound is reached (YES at step S309), the output controller 226 ends the output of the sound (step S310).

After performing the process at step S308, the NO process at step S307 or the process at step S310, the output controller 226 determines whether it is time to end the display of the image on the display screen 101S (step S311). At step S311, the output controller 226, for example, performs determination based on the management timer. On determining that it is time to end the display of the image (YES at step S311), the output controller 226 ends the display of the image (step S312). On determining that it is not time to end the display of the image (NO at step S311), the output controller 226 causes the operations at and after step S302 to be performed repeatedly.

On ending the display of the image, the output controller 226 determines whether all the images are displayed (step S313). On determining that not all the images are displayed (NO at step S313), the output controller 226 causes the operations at and after step S301 to be performed repeatedly. On determining that all the images are displayed (YES t step S313), the output controller 226 ends the image sound output process.

Figure 24:
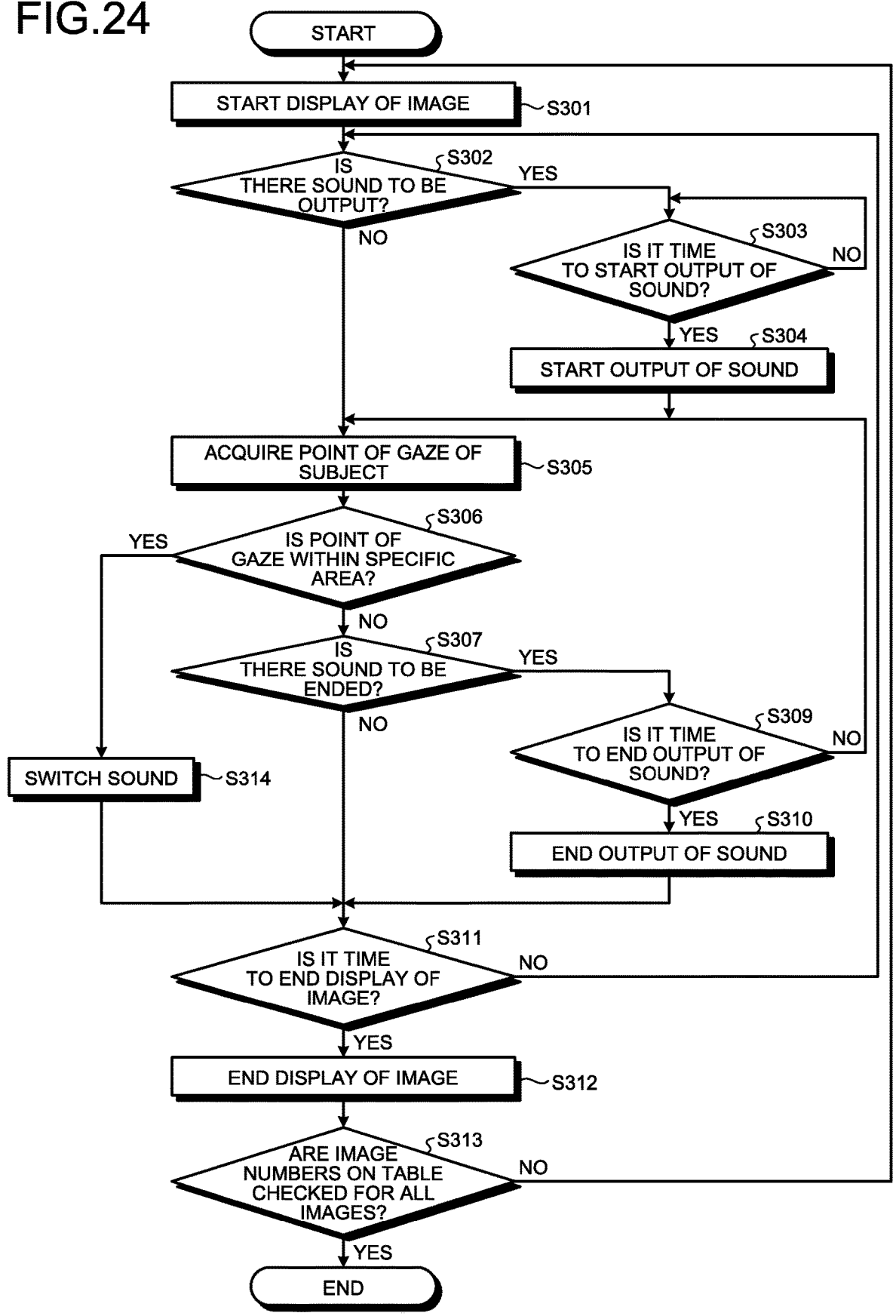
FIG. 24 is a flowchart illustrating another exemplary image sound output control process.

FIG. 24 is a flowchart illustrating another exemplary image sound output control process. FIG. 24 illustrates the exemplary case where the sound to be output is switched according to the positional data about the point of gaze of the subject. As illustrated in FIG. 24, when the sound to be output is switched according to the positional data about the point of gaze of the subject, only the process at step S308 illustrated in FIG. 23 differs and the processes from step S301 to step S307 and from step S309 to step S313 are the same.

In the example illustrated in FIG. 24, when the determination unit 218 determines that the point of gaze is within the specific area A at step S306, the output controller 226 performs the process of switching the sound to be output instead of step S308 (step S314). At step S314, the output controller 226 stops the output of the sound that is currently output and selects another sound instead of the sound that is currently output from among the multiple sounds stored in the storage unit 222. The output controller 226 then causes the sound output device 70 to output the selected sound. After performing step S314, the output controller 226 causes the process at and after step S311 to be performed. In the case where the determination unit 218 determines that the point of gaze is within the specific area A, when the process of changing the volume of the sound is performed, it suffices if the output controller 226 performs the process of changing the volume instead of step S308 in the flowchart illustrated in FIG. 24.

In the case where multiple sounds corresponding respectively to multiple specific areas AX (AX includes A1, A2 . . . ) are allocated and the determination unit 218 determines that the point of gaze is within a specific area AX, the output controller 226 may select a sound corresponding to the specific area AX from among the allocated multiple sounds and cause the sound output device 70 to output the sound.

The sound corresponding to the specific area A is not limited to one. Multiple sounds may be allocated and, when the determination unit 218 determines that the point of gaze is within the specific area A, the output controller 226 may select a sound from the allocated multiple sounds randomly and cause the sound output device 70 to output the sound. When a given order is set for the multiple sounds and the determination unit 218 determines that the point of gaze is within the specific area A1, the output controller 226 may select the sound following the sound being reproduced according to the given order and, when the determination unit 218 determines that the point of gaze is within the specific area A2, the output controller 226 may select the sound being reproduced or the former sound according to the given order and cause the sound output device 70 to output the sound.

Figure 25:
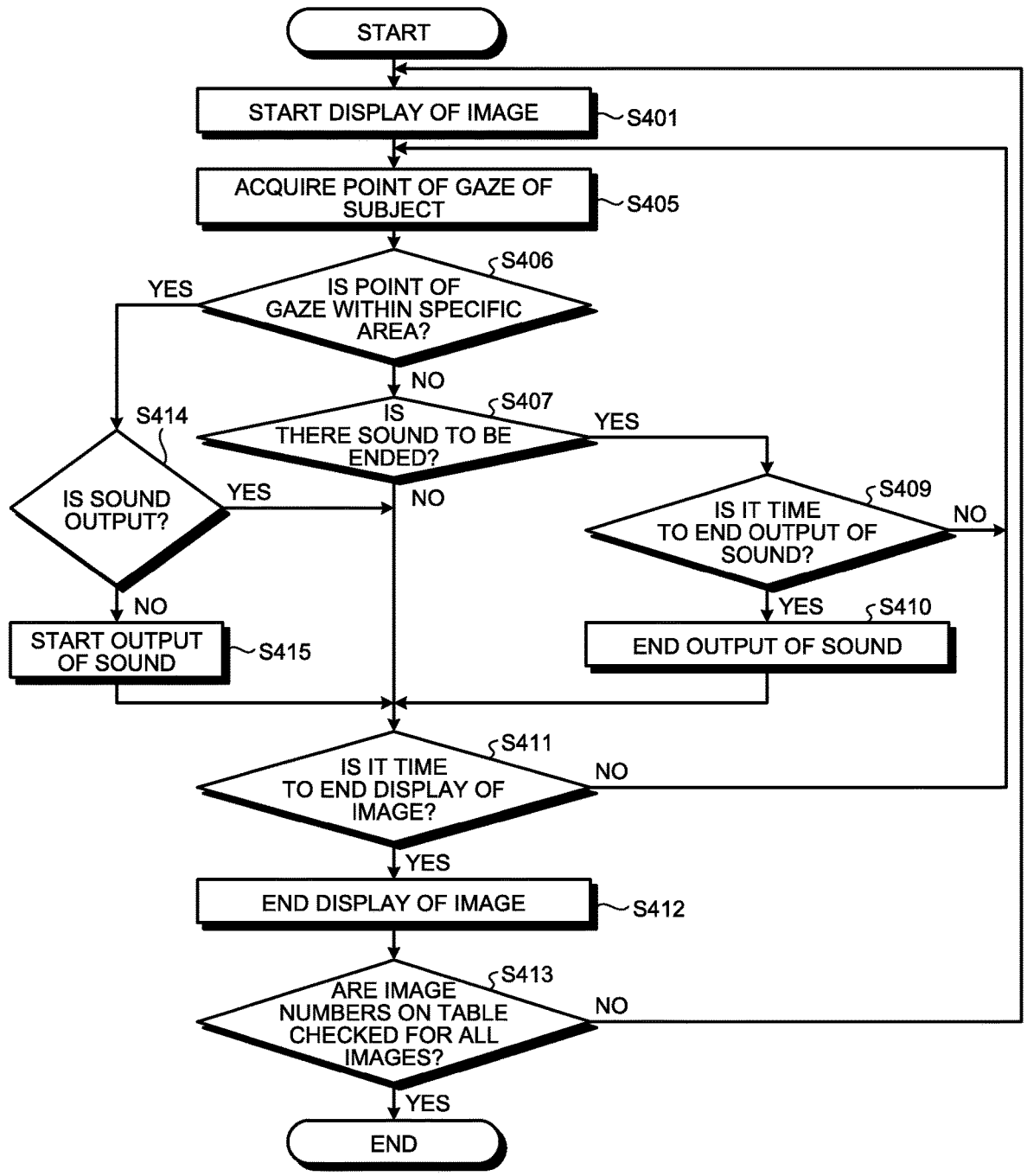
FIG. 25 is a flowchart illustrating another exemplary image sound output control process.

FIG. 25 is a flowchart illustrating another exemplary image sound output control process. FIG. 25 illustrates the exemplary case where the sound output is started according to the positional data about the point of gaze of the subject. In the example illustrated in FIG. 25, the processes at step S401, from step S405 to step S407, and from step S409 to step S413 are the same as the processes at step S301, from step S305 to step S307 and from step S309 to step S313 in FIG. 23. In the example illustrated in FIG. 25, the process corresponding to steps S302 to S304 in FIG. 23 is not performed and the process at step S405 is performed after step S401.

In the example illustrated in FIG. 25, when the determination unit 218 determines that the point of gaze is within the specific area A, the output controller 226 determines whether a sound is output (step S414). On determining that no sound is output (NO at step S414), the output controller 226 performs a process to start output of a sound (step S415) and moves to step S411. On determining that a sound is output (YES at step S414), the output controller 226 does not perform the process at step S415 and moves to step S411. When the output of the sound is stopped (suspended), the output is restarted in the same manner. In this case, determination on whether the output of the sound is stopped is made as the process corresponding to step S414. A process of restarting the output of the sound is performed as a process corresponding to step S415.

FIG. 26 is a flowchart illustrating another exemplary image sound output control process. FIG. 26 illustrates the exemplary case where, after the output of a sound is ended according to the positional data about the point of gaze of the subject, the timing of ending display of the image is controlled. In the example illustrated in FIG. 26, the process from step S501 to step S513 is the same as the process from step S301 to step S313 in FIG. 23.

In the example illustrated in FIG. 26, when the determination unit 218 determines that the point of gaze is within the specific area A, the output controller 226 ends the output of the sound as at step S308 in FIG. 23 (step S508). The output controller 226 determines whether to end the display of the image (step S514). At step S514, when the output controller 226 determines to end the display of the image (YES at step S514), the output controller 226 moves to step S512 to end the display of the image. In this case, even when the timing of ending the display, which is set previously, is not reached, the display of the image ends. Accordingly, the pre-set timing of ending the display is changed. When the output controller 226 determines not to end the display of the image at step S514, the output controller 226 causes the process at and after step S511 to be performed.

In the example illustrated in FIG. 26, when the determination unit 218 determines that the point of gaze is within the specific area A, the output controller 226 may perform the process at step S514 without performing step S508. In this case, with the sound being output, the display of the image may be ended.

As described above, the gaze detection device 100 according to the embodiment includes the display screen 101S that displays an image; the sound output device 70 that outputs a sound; the gaze point detector 214 that detects a position of a point of gaze of an observer observing the display screen 101S; the area setting unit 216 that sets a specific area A on part of the display screen 101S or of the image; the determination unit 218 that determines, when the specific area A is set on the display screen 101S or the image, whether the gaze point P is within the specific area A on the basis of the result of the detection of the position of the gaze point P; and the output controller 226 that causes the display screen 101S to display the image, causes the sound output device 70 to output a sound and, when it is determined that the gaze point P is within the specific area A, adjusts at least the sound output mode.

According to the configuration, when it is determined that the gaze point P is within the specific area A, at least the sound output mode is adjusted and this makes it possible to efficiently adjust the timing of changing the sound output mode.

In the gaze detection device 100 according to the embodiment, adjusting the sound output mode includes any one of stopping or ending the output of the sound, restarting the output of the sound from the mode in which the output is stopped, and adjusting the volume of the sound. The output controller 226 selects a sound from among the multiple sounds and causes the sound output device 70 to output the sound and adjusting the sound output mode includes switching the sound that is selected. Accordingly, it is possible to adjust the sound output mode widely.

In the gaze detection device 100 according to the embodiment, when it is determined that the point of gaze is within the specific area A, the output controller 226 controls the timing of ending display of the image. Accordingly, it is possible to control the timing of ending display of the image according to the change of the sound output mode.

In the gaze detection device 100 according to the embodiment, controlling the timing of ending the display includes changing the pre-set timing of ending the display. Accordingly, it is possible to flexibly adjust the timing of ending display of an image according to the timing of ending output of a sound.

Electronic Terminal

FIG. 27 is a diagram illustrating an electronic terminal 500 that is another exemplary image sound output device according to the embodiment. As illustrated in FIG. 27, the electronic terminal 500 includes portable electronic devices, such as tablet computers and smartphones. The electronic terminal 500 includes a housing 501, a display screen 502, an imaging device 503, a sound output device 504 and a control device 505.

The housing 501 holds the display screen 502, the imaging device 503, the sound output device 504 and the control device 505. The display screen 502 displays an image. The imaging device 503 is able to image the face of an observer observing the displays screen. The imaging device 503 is thus able to acquire image data about the eyeballs of the observer observing the display screen 502. The sound output device 504 outputs a sound.

The control device 505 controls operations of the display screen 502, the imaging device 503 and the sound output device 504. The control device 505 includes a microprocessor, such as a CPU, a memory, such as a ROM and a RAM, or a storage.

The control device 505 includes a gaze point detector that detects the position of a point of gaze of the observer on the basis of the image data of the eyeballs of the observer imaged by the imaging device 503; an area setting unit that sets specific areas 502a and 502b on part of the image displayed on the display screen 502; a determination unit that, when the image on which the specific areas 502a and 502b are set is displayed on the display screen 502, determines whether a gaze point P is within the specific area 502a or 502b on the basis of a result of detecting the position of the point of gaze; and an output controller that causes the display screen 502 to display an image, causes the sound output device 504 to output a sound, and, when it is determined that the gaze point P is within the specific area 502a or 502b, adjusts at least the sound output mode.

The control device 505 includes a storage unit. The storage unit stores, for example, data of images to be displayed on the display screen 502 and data of sounds to be output by the sound output device 504. The storage unit further stores an image sound output program that causes a computer to execute: causing the display screen to display an image; causing the sound output device to output a sound; detecting the position of a point of gaze of the observer observing the display screen; setting a specific area on part of the image displayed on the display screen; when the image on which the specific area is set is displayed on the display screen, determining whether the point of gaze is within the specific area on the basis of a result of detecting the position of the point of gaze; and adjusting at least the sound output mode when it is determined that the point of gaze is within the specific area.

In the electronic terminal 500, the control device 505 causes the display screen 502 to display the image. The control device 505 sets the specific areas 502a and 502b on part of the image displayed on the display screen 502. It is possible to set an appearance corresponding to the changed content of the sound output mode, which will be described below, for the appearance of the specific areas 502a and 502b. For example, the control device 505 is able to display a mark to reproduce a sound on the specific area 502a. The control device 505 is able to further display a mark to stop reproduction of the sound on the specific area 502b.

The control device 505 images the observer observing the display screen 502 with the imaging device 503 and acquires image data about the eyeballs of the observer. The control device 505 then detects the position of a point of gaze of the observer on the basis of the acquired image data.

The control device 505 determines whether the detected point of gaze is within the specific area 502a or 502b. On determining that the gaze point P of the observer is within the specific area 502a for example, the control device 505 performs, as the process of adjusting the sound output mode, a process of starting output of a sound or a process of restarting the output of the sound stopped from being output. On determining that the gaze point P of the observer is, for example, within the specific area 502a, the control device 505 performs the process of stopping the output of the sound as the process of adjusting the sound output mode. The content of adjusting the sound output mode is not limited to the above-described one. Adjusting the sound output mode includes, for example, any one of stopping or ending the output of the sound, restarting the output of the sound from the mode in which the output is stopped, and adjusting the volume of the sound. When the control device 505 selects a sound from the multiple sounds and causes the sound output device 504 to output the sound, adjusting the sound output mode includes switching the sound that is selected.

When it is determined that the point of gaze is within the specific area, the control device 505 may control the timing of ending display of the image.

As described above, not only in the gaze detection device 100, but also in the electronic terminal 500 that is the image sound output device that outputs an image and a sound, when it is determined that the gaze point P is within the specific area 502a or 502b, at least the sound output mode is adjusted and this enables efficient adjustment on the timing of changing the sound output mode.

The scope of the technology of the present disclosure is not limited to the above-described embodiment and modifications may be added within the scope of the disclosure.

The embodiment describes that the image and the sound are separated from each other. Alternatively, the image and the sound may be multiplexed. For example, when the image and the sound are multiplexed, step S206 is integrated with step S204 and step S208 is integrated with step S206 in FIG. 22. Whether to change the sound output mode is determined at step S204 and the image and sound output mode are changed at step S206.

According to the embodiment, it is possible to efficiently adjust the timing of changing the sound output mode.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An image sound output device comprising:
a display screen configured to display a first image on a display screen;
a sound output device configured to output a first sound;
a gaze point detector configured to detect a position of a point of gaze of an observer observing the display screen;
an area setting unit configured to set a specific area on part of the first image;
a determination unit configured to, while the specific area is set on the first image, determine whether the point of gaze is within the specific area based on a result of the detecting the position of the point of gaze;
a storage unit configured to store data setting an output timing of the first image and the first sound; and
an output controller configured to cause the display screen to display the first image and cause the first sound output device to output the first sound based on the data stored in the storage unit and, in response to determining that the point of gaze is within the specific area of the first image, stop outputting the first image or the first sound that is being output, and output a second image or a second sound that is defined by the data stored in the storage unit to be output subsequent to the first image or the first sound.

2. An image sound outputting method, comprising:
causing a display screen to display a first image;
causing a sound output device to output a first sound;
detecting a position of a point of gaze of an observer observing the display screen;
setting a specific area on part of the first image;
while the specific area is set on the first image, determining whether the point of gaze is within the specific area based a result of the detecting the position of the point of gaze;
storing, in a storage unit, data that sets an output timing of the first image and the first sound; and
in response to determining that the point of gaze is within the specific area of the first image, stop outputting the first image or the first sound that is being output, and output a second image or a second sound that is defined by the data stored in the storage unit to be output subsequent to the first image or the first sound.

3. A non-transitory computer readable recording medium storing therein an image sound output program that causes a computer to execute a process comprising:
causing a display screen to display a first image;
causing a sound output device to output a first sound;
detecting a position of a point of gaze of an observer observing the display screen;
setting a specific area on part of the first image;
while the specific area is set on the first image, determining whether the point of gaze is within the specific area based on a result of the detecting the position of the point of gaze;
storing, in a storage unit, data defining an output timing of the first image and the first sound; and
in response to determining that the point of gaze is within the specific area of the first image, stop outputting the first image or the first sound that is being output, and output a second image or a second sound that is defined by the data stored in the storage unit to be output subsequent to the first image or the first sound.

* * * * *